(12) United States Patent
Liu

(10) Patent No.: US 7,723,372 B2
(45) Date of Patent: May 25, 2010

(54) SPIROINDOLINONE DERIVATIVES

(75) Inventor: Jin-Jun Liu, Warren Township, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/372,926

(22) Filed: Feb. 18, 2009

(65) Prior Publication Data

US 2009/0239889 A1 Sep. 24, 2009

Related U.S. Application Data

(60) Provisional application No. 61/037,799, filed on Mar. 19, 2008.

(51) Int. Cl.
*C07D 413/02* (2006.01)
*C07D 405/02* (2006.01)
*C07D 209/96* (2006.01)
*C07D 401/02* (2006.01)
*A61K 31/4439* (2006.01)
*A61K 31/454* (2006.01)
*A61K 31/422* (2006.01)
*A61K 31/404* (2006.01)

(52) U.S. Cl. .................. 514/409; 514/378; 514/278; 548/247; 548/411; 546/15

(58) Field of Classification Search .................. 548/486
See application file for complete search history.

(56) References Cited

U.S. PATENT DOCUMENTS

| 5,114,937 | A * | 5/1992 | Hamby et al. ............. 514/238.2 |
| 7,495,007 | B2 * | 2/2009 | Chen et al. ..................... 514/278 |
| 2007/0213341 | A1 * | 9/2007 | Chen et al. ............. 514/253.03 |
| 2008/0114013 | A1 | 5/2008 | Liu et al. |
| 2008/0188506 | A1 | 8/2008 | Ding et al. |
| 2008/0287421 | A1 | 11/2008 | Liu et al. |

2008/0293723 A1 11/2008 Liu et al.

FOREIGN PATENT DOCUMENTS

WO WO 97/15556 5/1997
WO WO 2008/055812 5/2008

OTHER PUBLICATIONS

Patani et al. Chem. Rev. 1996, 96, 3147-3176.*
Kornberg et al. Bioorganic & Medicinal Chemistry Letters 1993, 3, 1257-1262.*
Ashimori A., et al. *Journal of Organic Chemistry* 57: 17 (2002) 4571-4572 XP002527583.
Ashimori A., et al. *Journal of the American Chemical Society* 120 (1998) 6477-6487 XP001038246.
Johnson R. S., et al. *Journal of the Chemical Society* (1900) 796-800 XP002156747.
Ding Ke, et al. *Journal of the American Chemical Society* 127:29 (2005) 10130-10131 XP002527584.

* cited by examiner

*Primary Examiner*—Rebecca L Anderson
*Assistant Examiner*—Matthew P Coughlin
(74) *Attorney, Agent, or Firm*—George W. Johnston; Patricia S. Rocha-Tramaloni

(57) ABSTRACT

There are provided compounds of the general formulas

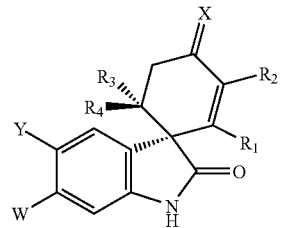

wherein W, X, Y, $R_1$, $R_2$, $R_3$, and $R_4$ are as described herein. The compounds exhibit anticancer activity.

9 Claims, No Drawings

SPIROINDOLINONE DERIVATIVES

PRIORITY OF RELATED APPLICATION(S)

This application claims the benefit of U.S. Provisional Application No. 61/037,799, filed Mar. 19, 2008, which is hereby incorporated by reference in its entirety.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention relates to oxindole derivatives which act as antagonists of mdm2 interactions and hence are useful as potent and selective anticancer agents. The present compounds are of the general formulas

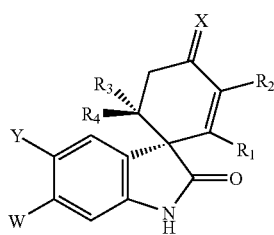

wherein W, X, Y, $R_1$, $R_2$, $R_3$ and $R_4$ are as described herein and pharmaceutically acceptable salts and esters thereof.

DETAILED DESCRIPTION OF THE INVENTION

There are provided compounds of the formula

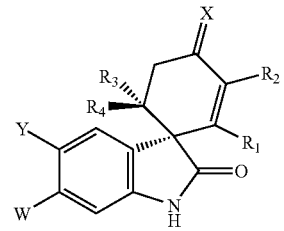

wherein
X is oxygen or hydrogen/hydroxy,
W is selected from the group consisting of hydrogen, halogen, cyano, nitro, ethynyl and cyclopropyl,
Y is hydrogen or fluorine
$R_1$, $R_2$, $R_3$ and $R_4$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl and substituted cycloalkenyl, with the proviso that one of $R_1/R_2$ or $R_3/R_4$ is hydrogen and the other is not hydrogen, or a pharmaceutically acceptable salt or ester thereof.
Preferred are compounds of formula I wherein
W is halogen
X is oxygen,
Y is hydrogen,
$R_1$ is hydrogen,
$R_4$ is hydrogen,
$R_2$ and $R_3$ are selected from the group consisting of lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl.

Further preferred are compounds of formula I wherein
W is chlorine
X is oxygen,
Y is hydrogen,
$R_1$ is hydrogen,
$R_4$ is hydrogen,
$R_3$ is a meta-halogen substituted phenyl with or without further substitution and $R_2$ is selected from the group consisting of lower alkyl, lower alkenyl, aryl, and substituted aryl.
Especially preferred are compounds selected from the group consisting of
rac-(1R,6S)-3-bromo-6'-chloro-6-(3-chlorophenyl)spiro[2-cyclohexene-1,3'-[3H]indole]-2',4(1'H)-dione,
rac-(1R,6S)-6'-chloro-6-(3-chlorophenyl)3-iodospiro[2-cyclohexene-1,3'-[3H]indole]-2',4(1'H)-dione,
rac-(1R, 4S, 6S)-6'-chloro-6-(3-chlorophenyl)-4-hydroxy-3-iodospiro[2-cyclohexene-1,3'-[3H]indol]-2'(1'H)-one,
rac-(1R, 4S, 6S)-6'-chloro-6-(3-chlorophenyl)-3-(5-fluoro-2-methylphenyl)-4-hydroxyspiro[2-cyclohexene-1,3'-[3H]indol]-2'(1'H)-one,
rac-(1R,6S)-6'-chloro-6-(3-chlorophenyl)-3-methylspiro[2-cyclohexene-1,3'-[3H]indole]-2',4(1'H)-dione,
rac-(1R,6S)-6'-chloro-6-(3-chlorophenyl)-3-(E)-(1-propenyl)spiro[2-cyclohexene-1,3'-[3H]indole]-2',4(1'H)-dione, rac-(1S,6S)-6'-chloro-6-(3-chlorophenyl)-2-(E)-(1-propenyl)spiro[2-cyclohexene-1,3'-[3H]indole]-2',4(1'H)-dione,
rac-(1S,6S)-6'-chloro-6-(3-chlorophenyl)-2-(methylethenyl)spiro[2-cyclohexene-1,3'-[3H]indole]-2',4(1'H)-dione,
rac-(1R,6S)-6'-chloro-6-(3-chlorophenyl)-3-(methylethenyl)spiro[2-cyclohexene-1,3'-[3H]indole]-2',4(1'H)-dione,
rac-(1R, 4S, 6S)-6'-chloro-6-(3-chlorophenyl)-3-(1,2-dimethyl-1-propenyl)-4-hydroxyspiro[2-cyclohexene-1,3'-[3H]indol]-2'(1'H)-one,
rac-(1R,6S)-6'-chloro-6-(3-chlorophenyl)-3-(1,2-dimethyl-1-propenyl)spiro[2-cyclohexene-1,3'-[3H]indole]-2',4(1'H)-dione,
rac-(1S,6S)-6'-chloro-6-(3-chlorophenyl)-2-(3-methoxyphenyl)spiro[2-cyclohexene-1,3'-[3H]indole]-2',4(1'H)-dione,
rac-(1R,6S)-6'-chloro-6-(3-chlorophenyl)-3-(3-methoxyphenyl)spiro[2-cyclohexene-1,3'-[3H]indole]-2',4(1'H)-dione,
rac-(1S,6S)-6'-chloro-6-(3-chlorophenyl)-2-(2-ethoxyphenyl)spiro[2-cyclohexene-1,3'-[3H]indole]-2',4(1'H)-dione,
rac-(1R,6S)-6'-chloro-6-(3-chlorophenyl)-3-(2-ethoxyphenyl)spiro[2-cyclohexene-1,3'-[3H]indole]-2',4(1'H)-dione,
rac-(1R, 4S, 6S)-6'-chloro-6-(3-chlorophenyl)-3-(2-methoxyphenyl)-4-hydroxyspiro[2-cyclohexene-1,3'-[3H]indol]-2'(1'H)-one,
rac-(1R,6S)-6'-chloro-6-(3-chlorophenyl)-3-(2-methoxyphenyl)spiro[2-cyclohexene-1,3'-[3H]indole]-2',4(1'H)-dione,
rac-(1S,6S)-6'-chloro-6-(3-chlorophenyl)-2-(2-methoxyphenyl)spiro[2-cyclohexene-1,3'-[3H]indole]-2',4(1'H)-dione,
rac-(1S,6S)-6'-chloro-6-(3-chlorophenyl)-2-(4-methoxyphenyl)spiro[2-cyclohexene-1,3'-[3H]indole]-2',4(1'H)-dione,
rac-(1R,6S)-6'-chloro-6-(3-chlorophenyl)-3-(4-methoxyphenyl)spiro[2-cyclohexene-1,3'-[3H]indole]-2',4(1'H)-dione,
rac-(1S,6S)-6'-chloro-6-(3-chlorophenyl)-2-(2-ethoxyphenyl)spiro[2-cyclohexene-1,3'-[3H]indole]-2',4(1'H)-dione,
rac-(1R,6S)-6'-chloro-6-(3-chlorophenyl)-3-(5-fluoro-2-methylphenyl)spiro[2-cyclohexene-1,3'-[3H]indole]-2',4(1'H)-dione,
(1R,6S)-6'-chloro-6-(3-chlorophenyl)-3-(2-methoxyphenyl)spiro[2-cyclohexene-1,3'-[3H]indole]-2',4(1'H)-dione,
(1S,6R)-6'-chloro-6-(3-chlorophenyl)-3-(2-methoxyphenyl)spiro[2-cyclohexene-1,3'-[3H]indole]-2',4(1'H)-dione,
rac-(1R,6S)-6'-chloro-6-(3-chlorophenyl)-3-(5-fluoro-2-hydroxyphenyl)spiro[2-cyclohexene-1,3'-[3H]indole]-2',4(1'H)-dione,
rac-(1R,6S)-6'-chloro-6-(3-chlorophenyl)-3-(4-fluoro-2-hydroxyphenyl)spiro[2-cyclohexene-1,3'-[3H]indole]-2',4(1'H)-dione,
rac-(1R,6S)-6'-chloro-3-(5-chloro-2-ethoxyphenyl)-6-(3-chlorophenyl)spiro[2-cyclohexene-1,3'-[3H]indole]-2',4(1'H)-dione,
rac-(1R,6S)-6'-chloro-6-(3-chlorophenyl)-3-(2-phenoxyphenyl)spiro[2-cyclohexene-1,3'-[3H]indole]-2',4(1'H)-dione,
rac-(1R,6S)-6'-chloro-3-(4-chloro-2-ethoxyphenyl)-6-(3-chlorophenyl)spiro[2-cyclohexene-1,3'-[3H]indole]-2',4(1'H)-dione,
rac-(1R,6S)-6'-chloro-3-(4-chloro-2-methoxyphenyl)-6-(3-chlorophenyl)spiro[2-cyclohexene-1,3'-[3H]indole]-2',4(1'H)-dione,
rac-(1R,6S)-6'-chloro-6-(3-chlorophenyl)-3-(2-ethoxy-5-methylphenyl)spiro[2-cyclohexene-1,3'-[3H]indole]-2',4(1'H)-dione,
rac-(1R,6S)-6'-chloro-6-(3-chlorophenyl)-3-[2-(trifluoromethoxy)phenyl)]spiro[2-cyclohexene-1,3'-[3H]indole]-2',4(1'H)-dione,
rac-(1R,6S)-6'-chloro-6-(3-chlorophenyl)-3-(3-furanyl)spiro[2-cyclohexene-1,3'-[3H]indole]-2',4(1'H)-dione,
rac-(1R,6S)-6'-chloro-6-(3-chlorophenyl)-3-[4-(hydroxymethyl)phenyl]spiro[2-cyclohexene-1,3'-[3H]indole]-2',4(1'H)-dione,
rac-(1R,6S)-6'-chloro-6-(3-chlorophenyl)-3-(3,5-dimethyl-4-isoxazolyl)spiro[2-cyclohexene-1,3'-[3H]indole]-2',4(1'H)-dione
rac-(1R,6S)-6'-chloro-6-(3-chlorophenyl)-3-(1-cyclohexenyl)spiro[2-cyclohexene-1,3'-[3H]indole]-2',4(1'H)-dione,
rac-(1R,6S)-6'-chloro-6-(3-chlorophenyl)-3-[2-(hydroxymethyl)phenyl]spiro[2-cyclohexene-1,3'-[3H]indole]-2',4(1'H)-dione,
rac-(1R,6S)-6'-chloro-6-(3-chlorophenyl)-3-[3-(hydroxymethyl)phenyl]spiro[2-cyclohexene-1,3'-[3H]indole]-2',4(1'H)-dione,
rac-(1S,6S)-6'-chloro-6-(3-chlorophenyl)-2-[3-(methoxycarbonyl)phenyl]spiro[2-cyclohexene-1,3'-[3H]indole]-2',4(1'H)-dione,
rac-(1R,6S)-6'-chloro-6-(3-chlorophenyl)-3-[3-(methoxycarbonyl)phenyl)]spiro[2-cyclohexene-1,3'-[3H]indole]-2',4(1'H)-dione,
rac-(1R,6S)-6'-chloro-6-(3-chlorophenyl)-2-[4-(methoxycarbonyl)phenyl]spiro[2-cyclohexene-1,3'-[3H]indole]-2',4(1'H)-dione,
rac-(1R,6S)-6'-chloro-6-(3-chlorophenyl)-3-[4-(methoxycarbonyl)phenyl]spiro[2-cyclohexene-1,3'-[3H]indole]-2',4(1'H)-dione,
rac-(1R,6S)-6'-chloro-3-(3-carboxyphenyl)-6-(3-chlorophenyl)spiro[2-cyclohexene-1,3'-[3H]indole]-2',4(1'H)-dione,
rac-(1S,6S)-6'-chloro-6-(3-chlorophenyl)-2-(3-cyanophenyl)spiro[2-cyclohexene-1,3'-[3H]indole]-2',4(1'H)-dione,
rac-(1R,6S)-6'-chloro-6-(3-chlorophenyl)-3-(3-cyanophenyl)spiro[2-cyclohexene-1,3'-[3H]indole]-2',4(1'H)-dione,
rac-(1R,6S)-6'-chloro-6-(3-chlorophenyl)-2-(3-propoxyphenyl)spiro[2-cyclohexene-1,3'-[3H]indole]-2',4(1'H)-dione,
rac-(1R,6S)-6'-chloro-6-(3-chlorophenyl)-3-(3-propoxyphenyl)spiro[2-cyclohexene-1,3'-[3H]indole]-2',4(1'H)-dione,
rac-(1R,6S)-6'-chloro-6-(3-chlorophenyl)-3-(3-methyl-5-t-butylphenyl)spiro[2-cyclohexene-1,3'-[3H]indole]-2',4(1'H)-dione,
rac-(1R,6S)-6'-chloro-6-(3-chlorophenyl)-3-(2,4,6-trimethylphenyl)spiro[2-cyclohexene-1,3'-[3H]indole]-2',4(1'H)-dione,
rac-(1R,6S)-6'-chloro-6-(3-chlorophenyl)-3-(4-t-butylphenyl)spiro[2-cyclohexene-1,3'-[3H]indole]-2',4(1'H)-dione,
rac-(1R,6S)-6'-chloro-6-(3-chlorophenyl)-2-(2-methoxy-3-pyridyl)spiro[2-cyclohexene-1,3'-[3H]indole]-2',4(1'H)-dione, rac-(1R,6S)-6'-chloro-6-(3-chlorophenyl)-3-(2-methoxy-3-pyridyl)spiro[2-cyclohexene-1,3'-[3H]indole]-2',4(1'H)-dione, rac-(1R,6S)-6'-chloro-6-(3-chlorophenyl)-3-(3-BOC-aminophenyl)spiro[2-cyclohexene-1,3'-[3H]indole]-2',4(1'H)-dione, rac-(1R,6S)-6'-chloro-6-(3-chlorophenyl)-2-(2,6-dihydro-2H-BOC-pyridyl)spiro[2-cyclohexene-1,3'-[3H]indole]-2',4(1'H)-dione, rac-(1R,6S)-6'-chloro-6-(3-chlorophenyl)-3-(2,6-dihydro-2H-BOC-pyridyl)spiro[2-cyclohexene-1,3'-[3H]indole]-2',4(1'H)-dione, rac-(1R,6S)-6'-chloro-6-(3-chlorophenyl)-3-(2-formylphenyl)spiro[2-cyclohexene-1,3'-[3H]indole]-2',4(1'H)-dione, rac-(1R,6S)-6'-chloro-6-(3-chlorophenyl)-3-(3,5-bistrifluoromethylphenyl)spiro[2-cyclohexene-1,3'-[3H]indole]-2',4(1'H)-dione, rac-(1R,6S)-6'-chloro-6-(3-chlorophenyl)-2-(2-ethylenephenyl)spiro[2-cyclohexene-1,3'-[3H]indole]-2',4(1'H)-dione, rac-(1R,6S)-6'-chloro-6-(3-chlorophenyl)-2-(2-ethylenephenyl)spiro[2-cyclohexene-1,3'-[3H]indole]-2',4(1'H)-dione, rac-(1R,6S)-6'-chloro-6-(3-chlorophenyl)-2-(3-methylthiophenyl)spiro[2-cyclohexene-1,3'-[3H]indole]-2',4(1'H)-dione, rac-(1R,6S)-6'-chloro-6-(3-chlorophenyl)-3-(3-methylthiophenyl)spiro[2-cyclohexene-1,3'-[3H]indole]-2',4(1'H)-dione, rac-(1R,6S)-6'-chloro-6-(3-chlorophenyl)-2-(3-dimethylacetamidophenyl)spiro[2-cyclohexene-1,3'-[3H]indole]-2',4(1'H)-dione, rac-(1R,6S)-6'-chloro-6-(3-chlorophenyl)-3-(3-3-dimethylacetamido phenyl)spiro[2-cyclohexene-1,3'-[3H]indole]-2',4(1'H)-dione and rac-(1R,6S)-6'-chloro-6-(3-chlorophenyl)-3-(3,4-dimethylphenyl)spiro[2-cyclohexene-1,3'-[3H]indole]-2',4(1'H)-dione.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, carboxy, carboxy lower alkoxy and CN. Preferred substituents for alkyl are alkoxy and N(lower alkyl)$_2$.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 456-457.

The compounds of formula I as well as their salts that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in formula I above.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"IC50" refers to the concentration of a particular compound required to inhibit 50% of a specific measured activity. $IC_{50}$ can be measured, inter alia, as is described subsequently.

Synthetic Methods

The present invention provides methods for the synthesis of spiroindolinones. The compounds of the invention can be prepared by processes known in the art. Suitable processes for synthesizing these compounds are provided in the examples. Generally, the compounds of the invention can be prepared according to the synthesis schemes provided below.

The following synthetic schemes provide three general methods for preparation of compounds of the invention, i.e., compounds of formula I.

In method A, illustrated in scheme 1, a compound of formula IV is made from a Diels-Alder reaction of a compound of formula II with Danishefsky diene III at 140° C. followed by treatment with aq.NaOH in MeOH and pTsOH in toluene. A compound of formula IV is converted to compounds of formula Ia and Ib by reacting with $I_2$ or $PhNMe_3Br_3$ to form intermediate V followed by Suzuki coupling with various boronic acid in the presence of palladium catalysts.

Scheme 1

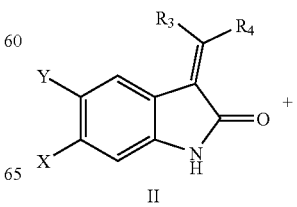

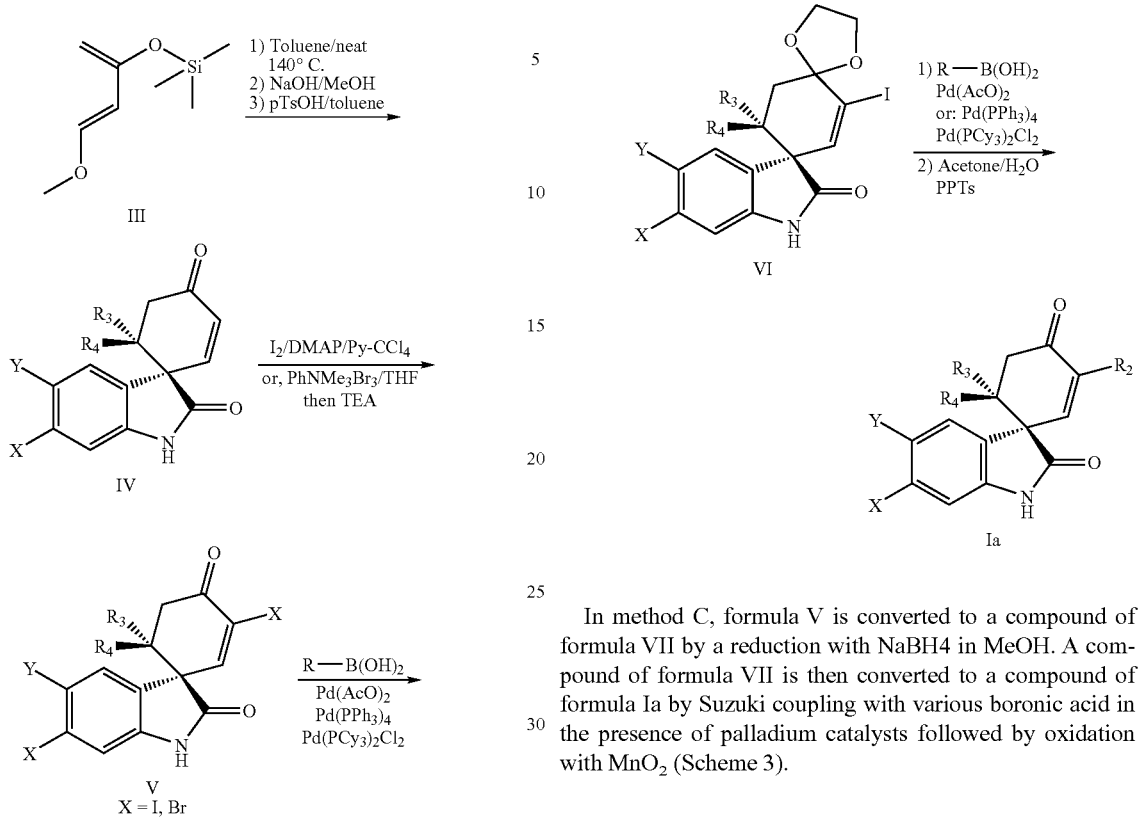

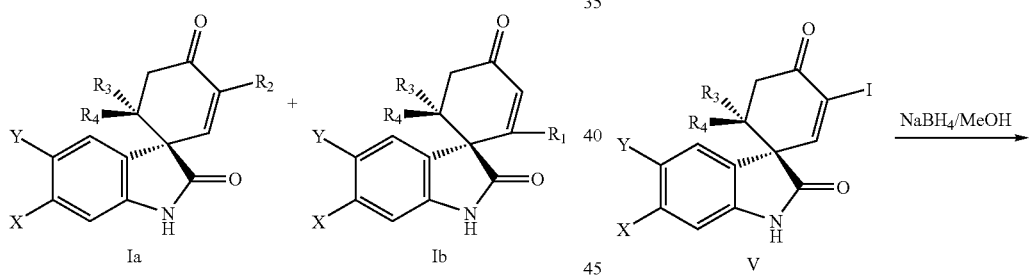

In method B, a protected form VI of formula V is converted to a compound of formula Ia by Suzuki coupling with various boronic acid in the presence of palladium catalysts followed by deprotection with acid. (Scheme 2).

In method C, formula V is converted to a compound of formula VII by a reduction with NaBH4 in MeOH. A compound of formula VII is then converted to a compound of formula Ia by Suzuki coupling with various boronic acid in the presence of palladium catalysts followed by oxidation with MnO$_2$ (Scheme 3).

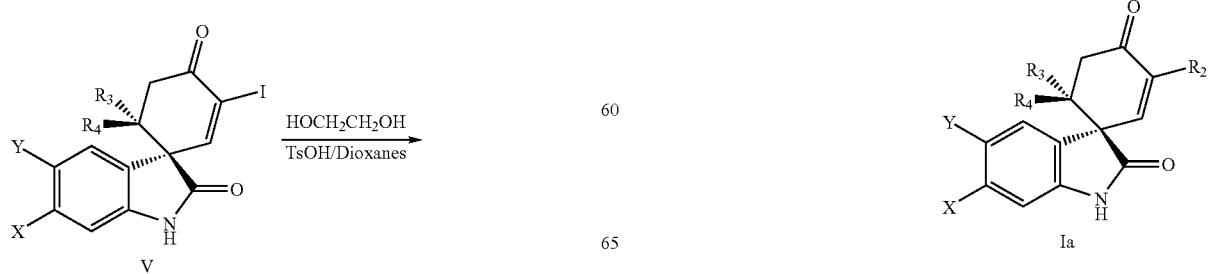

EXAMPLES

The compounds of the present invention may be synthesized according to known techniques. The following examples and references are provided to aid the understanding of the present invention, the true scope of which is set forth in the appended claims.

Example 1

General Synthesis Steps and Starting Materials

Example 1a

Preparation of intermediate E/Z-substituted-methylidene]-1,3-dihydro-indol-2-one II

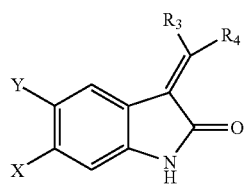

II

To the mixture of appropriate oxindole (92 mmol) and aldehyde (92 mmol) in methanol (100 mL) was added pyrrolidine (92 mmol) dropwise. The mixture was then heated at 70° C. for 3 h. After cooled to 4° C., the mixture was filtered and resulting precipitate was collected, dried to give a mixture of E/Z-substituted-methylidene]-1,3-dihydro-indol-2-one II (>90 %).

Example 1b

Preparation of Rac-spiro[5-cyclohexene-1,3'[3H] indole]2',4(1'H)-dione IV

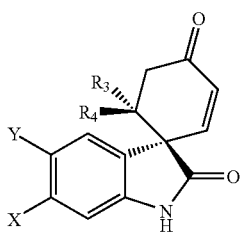

IX

To a suspension of E/Z-substituted-methylidene]-1,3-dihydro-indol-2-one VII (15.0 mmol) in toluene (50 mL) in a sealed tube was added (3-methoxy-1-methylene-allyloxy)-trimethyl-silane (3.44 g, 20.0 mmol). The reaction mixture was allowed to stir at 140° C. for 24 hrs. The solvent was removed by concentration. The residue was dissolved in MeOH (50 mL) and treated with 4N NaOH (5 mL) at rt for 2 hrs. The reaction mixture was then diluted with AcOEt and washed with water and brine. After concentration the residue was purified by flash column to give rac-(6-alkooxyspiro [cyclohexane-1,3'-[3H]indole]-2',4(1'H)-dione II and rac-spiro[5-cyclohexene-1,3'-[3H]indole]-2',4(1'H-dione IV

Example 1c

Preparation of rac-(1R,6S)-3-bromo-6'-chloro-6-(3-chlorophenyl)spiro[2-cyclohexene-1,3'-[3H]indole]-2',4(1'H)-dione from rac-spiro[5-cyclohexene-1,3'-[3H]indole]-2',4(1'H)-dione

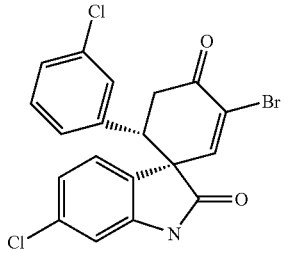

M. W. 437.12 $C_{19}H_{12}BrCl_2NO_2$

To a mixture of compound rac-spiro[5-cyclohexene-1,3'-[3H]indole]-2',4(1'H)-dione (179.1 mg, 0.5 mmol) in THF (2 mL) was added dropwise $PhNMe_3Br_3$ (212.4 mg, 0.55 mmol) in THF (1 mL) at −10° C. After stirring at room temperature overnight, TEA (75.8 mg, 0.75 mmol) was added cautiously. The reaction mixture was stirred at rt for 2 hrs and then diluted with AcOEt. The resulting solution was washed with water and brine. The organic layer was dried over $NaSO_4$. Concentration of the solvent gave the crude product which was purified by flash column ($SiO_2$, AcOEt/Hex=5% to 40%) to give rac-(1R,6S)-3-bromo-6'-chloro-6-(3-chlorophenyl)spiro[2-cyclohexene-1,3'-[3H]indole]-2',4(1'H)-dione (84.6 mg, 38.7%): HRMS (ES$^+$) m/z Calcd for $C_{19}H_{12}BrCl_2NO_2$+H [(M+H)$^+$]: 435.9501, found: 435.9500.

Example 1d

Preparation of rac-(1R,6S)-6'-chloro-6-(3-chlorophenyl)3-iodospiro[2-cyclohexene-1,3'-[3H]indole]-2',4 (1'H)-dione from rac-spiro[5-cyclohexene-1,3'-[3H] indole]-2',4(1'H)-dione

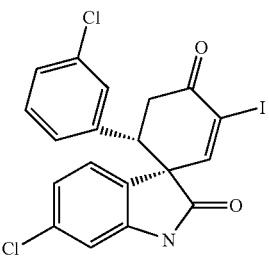

M. W. 484.12 $C_{19}H_{12}Cl_2INO_2$

A dark-brown colored solution of rac-spiro[5-cyclohexene-1,3'-[3H]indole]-2',4(1'H)-dione (2.14 g, 6.0 mmol), DMAP (0.15 g, 1.2 mmol), and $I_2$ (5.58 g, 18.0 mmol) in Py-$CCl_4$ (1/1, 40 mL) was stirred under $N_2$ atmosphere, in dark, heated at 50° C. The progress of the reaction was monitored by TLC (AcOEt/nHex=1/3). After 4 hrs, the reaction mixture was allowed to cool to rt, and then diluted with AcOEt. The resulting solution was washed with saturated aqueous sodium thiosulfate solution (3×30 mL) followed by washing with sat.CuSO$_4$ and brine. The organic layer was dried over Na$_2$SO$_4$. Concentration of the solvent gave the crude product (2.81 g, 96.9%), as a brown solid which was triturated with AcOEt and Hex to give rac-(1R,6S)-6'-Chloro-6-(3-chlorophenyl)3-iodospiro[2-cyclohexene-1,3'-[3H]indole]-2',4(1'H)-dione as an off-white solid (2.43 g, 83.7%) which is used in the next steps without further purification: HRMS (ES$^+$) m/z Calcd for $C_{19}H_{12}Cl_2INO_2$+H [(M+H)$^+$]: 483.9363, found: 483.9364.

Example 2

General Procedure for the Preparation of Compounds I

Method A

Preparation of compounds Ia and Ib from rac-(6-substituted)-3-iodospiro[2-cyclohexene-1,3'-[3H]indole]-2',4(1'H)-dione Via Suzuki Coupling Reaction with Boronic Acid

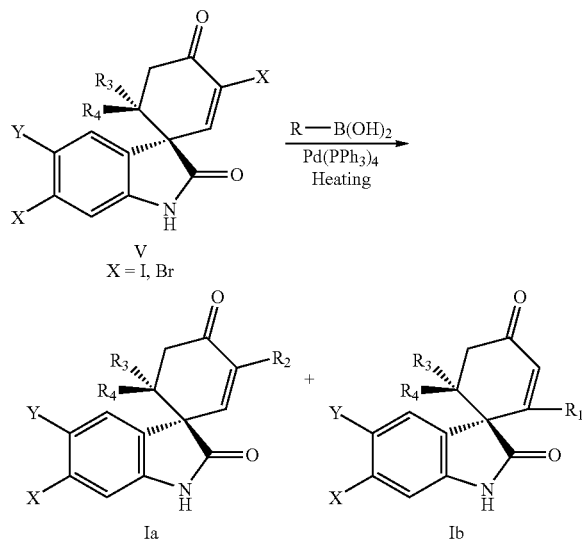

A suspension of appropriate rac-(6-substituted)-3-iodospiro[2-cyclohexene-1,3'-[3H]indole]-2',4(1'H)-dione V (1.0 mmol), Pd(PPh$_3$)$_4$ (0.08 mmol), Cs$_2$CO$_3$ (2.0 mmol) and boronic acid (2.0 mmol) in a mixture of THF (5 mL) and water (1 mL) in a sealed tube was heated to 90-110° C. overnight or to 120° C. for 15 min with microwave reactor. The reaction was quenched by adding Sat. NH$_4$Cl after cooled to rt. The reaction mixture was extracted with AcOEt and the organic layer was dried over Na$_2$SO$_4$. The solvent was removed by concentration. The residue was purified by flash column (5%-30% AcOEt in Hex) to give racemic forms of compound Ia and Ib, or a chiral column to give pure entantiomers of compound Ia and Ib.

Method B

Preparation of compounds Ia from rac-(6-substituted)-3-iodospiro[2-cyclohexene-1,3'-[3H]indole]-2',4(1'H)-dione V Via Intermediater VI (Scheme 2)

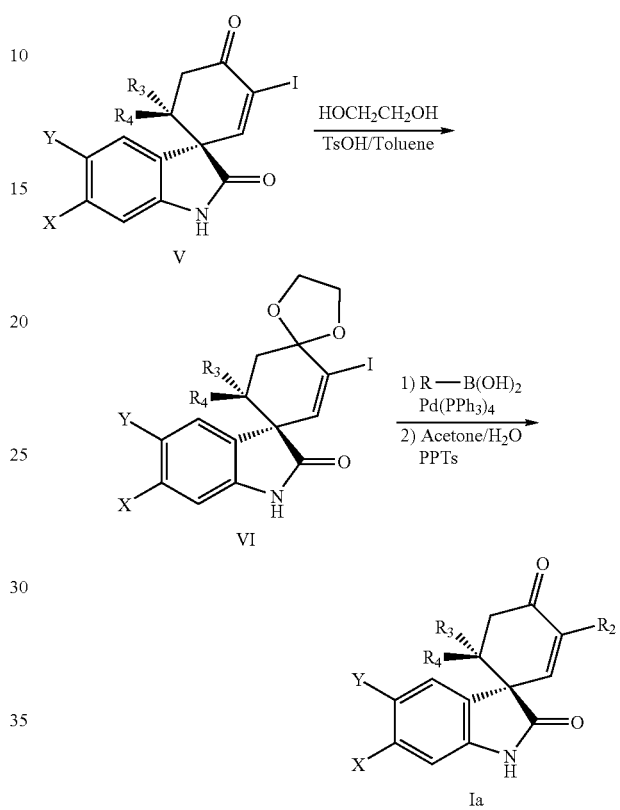

Step 1

A suspension of rac-(6-substituted)-3-iodospiro[2-cyclohexene-1,3'-[3H]indole]-2',4(1'H)-dione V (2.93 mmol), ethylene glycol (10 mL) and TsOH (0.53 mmol) in toluene (30 mL) was heated at 150° C. to reflux for 18 hrs with a Dean-Stark trap to remove water. The reaction was quenched by adding Sat. NaHCO$_3$ after cooled to rt. The reaction mixture was extracted with AcOEt and the organic layer was washed with water and brine. The solvent was removed by concentration to give the corresponding ketal VI which was used in the next step without further purification.

Step 2

A suspension of ketal VI (0.12 mmol), Pd(PPh$_3$)$_4$ (0.007 mmol), boronic acid (0.24 mmol) and cesium carbonate (0.24 mmol) in a mixture of THF (5 mL) and water (1 mL) in a sealed tube were heated with CEM microwave reactor to 120° C. for 15 min. The reaction was quenched with sat.NH$_4$Cl and extracted with AcOEt, dried over Na$_2$SO$_4$, evaporated under reduced pressure. The residue was then purified by flash column (AcOEt/Hex=1%-30%, 10 min) to give the corresponding coupling product which was used in the next step without further purification.

Step 3

To the solution of the above product (0.07 mmol) in acetone/H$_2$O (2.0 mL/0.2 mL) was added PPTs (cat.) and the reaction mixture were heated with microwave reactor to 120° C. for 10 min. The reaction was quenched with sat.NH$_4$Cl and extracted with AcOEt, dried over Na$_2$SO$_4$, evaporated under reduced pressure to give racemic forms of compound Ia.

Method C

Preparation of compounds Ia from rac-(6-substituted)-3-iodospiro[2-cyclohexene-1,3'-[3H]indole]-2',4(1'H)-dione V Via Intermediater VII (Scheme 3)

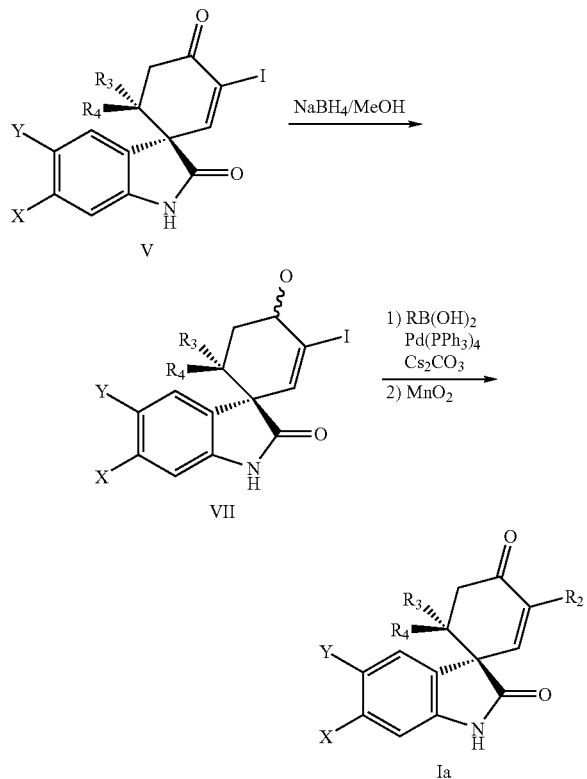

Step 1

To a solution of rac-(6-substituted)-3-iodospiro[2-cyclohexene-1,3'-[3H]indole]-2',4(1'H)-dione V (4.0 mmol) in MeOH (30 mL) was added NaBH$_4$ (8.0 mmol) in one portion and the reaction mixture was stirred at rt for 5 min. The mixture was poured into water and extracted with AcOEt, dried over Na$_2$SO$_4$, evaporated under reduced pressure column to give a mixture of the corresponding alcohol intermediater rac-(6-substituted)-4-hydroxy-3-iodospiro[2-cyclohexene-1,3'-[3H]indole]-2'(1'H)-one VII (100%) which was used in the next step without further purification.

Step 2

A suspension of appropriate rac-(6-substituted)-4-hydroxy-3-iodospiro[2-cyclohexene-1,3'-[3H]indol]-2'(1'H)-one (1.0 mmol), Pd(PPh$_3$)$_4$ (0.08 mmol), Cs$_2$CO$_3$ (2.0 mmol) and boronic acid (2.0 mmol) in a mixture of THF (5 mL) and water (1 mL) in a sealed tube was heated to 90-110° C. overnight or to 120° C. for 15 min with microwave reactor. The reaction was quenched by adding Sat. NH$_4$Cl after cooled to rt. The reaction mixture was extracted with AcOEt and the organic layer was dried over Na$_2$SO$_4$. The solvent was removed by concentration. The residue was purified by flash column (5% -30% AcOEt in Hex) to give rac-(6-substituted)-(3-substituted)-4-hydroxyspiro[2-cyclohexene-1,3'-[3H]indol]-2'(1'H)-one which was used in the next step without further purification.

Step 3

A mixture of rac-(6-substituted)-(3-substituted)-4-hydroxyspiro[2-cyclohexene-1,3'-[3H]indol]-2'(1'H)-one (0.47 mmol) and MnO$_2$ (11.5 mmol) in CH$_2$Cl$_2$ (20 mL) were heated to reflux for 16 hrs. The mixture was filtered through Celite and concentrated. The residue was then purified by flash column (AcOEt/Hex=1%-30%) to give racemic forms of compound Ia.

Example 3

Preparation of rac-(4'R,5'S)-6''-chloro-5'-(3-chlorophenyl)-2'-iododispiro[1,3-dioxolane-2,1'-[2]cyclohexene-4',3''-[3H]indol]-2''(1''H)-one

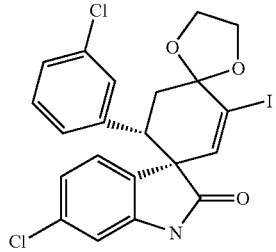

M. W 528.18 C$_{21}$H$_{16}$Cl$_2$INO$_3$

In a manner similar to the method described in example 2 (method B, step 1), rac-(1R,6S)-6'-chloro-6-(3-chlorophenyl)3-iodospiro[2-cyclohexene-1,3'-[3H]indol]-2',4(1'H)-dione (1.42 g, 2.93 mmol) was reacted with ethylene glycol (10 mL) and TsOH (0.53 mmol) in toluene (30 mL) at 150° C overnight to give rac-(4'R,5'S)-6''-chloro-5'-(3-chlorophenyl)-2'-iododispiro[1,3-dioxolane-2,1'-[2]cyclohexene-4',3''-[3H]indol]-2''(1H)-one (1.36 g, 87.7%) which was used in the next step without further purification.

Example 4

Preparation of rac-(1R, 4S, 6S)-6'-chloro-6-(3-chlorophenyl)-4-hydroxy-3-iodospiro[2-cyclohexene-1, 3'-[3H]indol]-2'(1'H)-one

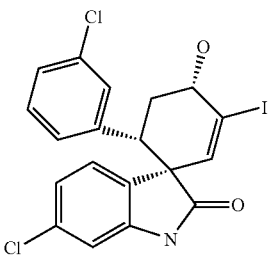

M. W. 486.12 C$_{19}$H$_{14}$Cl$_2$INO$_2$

In a manner similar to the method described in example 2 (method C, step 1), rac-(1R,6S)-6'-chloro-6-(3-chlorophenyl)3-iodospiro[2-cyclohexene-1,3'-[3H]indol]-2',4(1'H)-dione (1.94 g, 4.0 mmol) was reduced with NaBH4 (0.3 g, 8.0 mmol) in MeOH (30 mL) to give rac-(1R, 4S, 6S)-6'-chloro-6-(3-chlorophenyl)-4-hydroxy-3-iodospiro[2-cyclohexene-1,3'-[3H]indol]-2'(1'H)-one (1.94 g): HRMS (ES⁺) m/z Calcd for C₁₉H₁₄Cl₂INO₂+H [(M+H)⁺]: 485.9519, found: 485.9521.

Example 5

Preparation of rac-(1R, 4S, 6S)-6'-chloro-6-(3-chlorophenyl)-3-(5-fluoro-2-methylphenyl)-4-hydroxyspiro[2-cyclohexene-1,3'-[3H]indol]-2'(1'H)-one

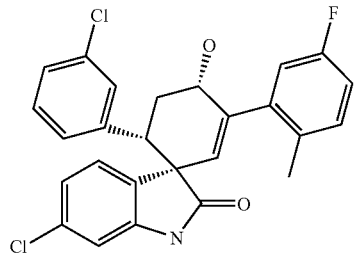

M. W. 415.3 C₂₂H₂₀Cl₂N₂O₂

In a manner similar to the method described in example 2 (method C, step 2), rac-(1R, 4S, 6S)-6'-chloro-6-(3-chlorophenyl)-4-hydroxy-3-iodospiro[2-cyclohexene-1,3'-[3H]indol]-2'(1'H)-one (48.6 mg, 0.1 mmol) was reacted with 5-fluoro-2-methylphenylboronic acid (30.8 mg, 0.2 mmol) in the presence of Pd(PPh₃)₄ (5.6 mg, 0.005 mmol), Cs₂CO₃ (130.0 mg, 0.4 mmol) in a mixture of THF (1.6 mL) and water (0.4 mL) in a sealed tube was heated to 120° C. for 10 min with microwave reactor to give rac-(1R, 4S, 6S)-6'-chloro-6-(3-chlorophenyl)-3-(5-fluoro-2-methylphenyl)-4-hydroxyspiro[2-cyclohexene-1,3'-[3H]indol]-2'(1'H)-one (32.8 mg, 70.1%): HRMS (ES⁺) m/z Calcd for C₂₆H₂₀Cl₂FNO₂+H [(M+H)⁺]: 468.0928, found: 468.0927.

Example 6

Preparation of rac-(1R,6S)-6'-chloro-6-(3-chlorophenyl)-3-(5-fluoro-2-methylphenyl)spiro[2-cyclohexene-1,3'-[3H]indole]-2',4(1'H)-dione

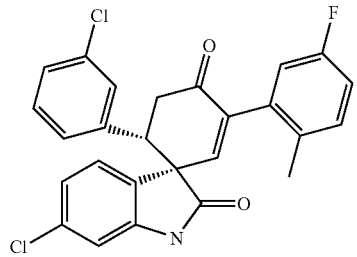

M. W. 466.3 C₂₆H₁₈Cl₂FNO₂

In a manner similar to the method described in example 2 (method C, step 3), rac-(1R, 4S, 6S)-6'-chloro-6-(3-chlorophenyl)-3-(5-fluoro-2-methylphenyl)-4-hydroxyspiro[2-cyclohexene-1,3'-[3H]indol]-2'(1'H)-one (32 mg, 0.068 mmol) was reacted with MnO₂ (200 mg) in CH₂Cl₂ (5 mL) were heated to reflux for 16 hrs to give rac-(1R,6S)-6'-Chloro-6-(3-chlorophenyl)-3-(5-fluoro-2-methylphenyl)spiro[2-cyclohexene-1,3'-[3H]indole]-2',4(1'H)-dione (27.5 mg, 86.2%): HRMS (ES⁺) m/z Calcd for C₂₆H₁₈Cl₂FNO₂+H [(M+H)⁺]: 466.0772, found 466.0771.

Example 7

Preparation of rac-(1R, 4S, 6S)-6'-chloro-6-(3-chlorophenyl)-3-(2-methoxyphenyl)-4-hydroxyspiro[2-cyclohexene-1,3'-[3H]indol]-2'(1'H)-one

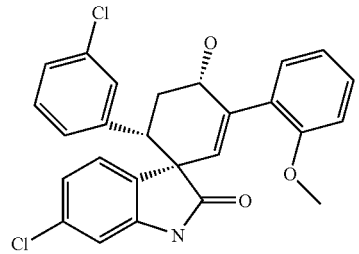

M. W. 466.4 C₂₆H₂₁Cl₂NO₃

In a manner similar to the method described in example 2 (method C, step 2), rac-(1R, 4S, 6S)-6'-chloro-6-(3-chlorophenyl)-4-hydroxy-3-iodospiro[2-cyclohexene-1,3'-[3H]indol]-2'(1'H)-one (48.6 mg, 0.1 mmol) was reacted with 5-fluro-2-methylphenylboronic acid (30.8 mg, 0.2 mmol) in the presence of Pd(PPh₃)₄ (5.6 mg, 0.005 mmol), Cs₂CO₃ (130.0 mg, 0.4 mmol) in a mixture of THF (1.6 mL) and water (0.4 mL) in a sealed tube was heated to 120° C. for 10 min with microwave reactor to give rac-(1R, 4S, 6S)-6'-chloro-6-(3-chlorophenyl)-3-(2-methoxyphenyl)-4-hydroxyspiro[2-cyclohexene-1,3'-[3H]indol]-2'(1'H)-one (32.8 mg, 70.1%): HRMS (ES⁺) m/z Calcd for C₂₆H₂₀Cl₂FNO₂+H [(M+H)⁺]: 468.0928, found: 468.0927.

Example 8

Preparation of rac-(1R,6S)-6'-chloro-6-(3-chlorophenyl)-3-(-2-methylphenyl)spiro[2-cyclohexene-1,3'-[3H]indole]-2',4(1'H)-dione, (1R,6S)-6'-Chloro-6-(3-chlorophenyl)-3-(2-methoxyphenyl)spiro[2-cyclohexene-1,3'-[3H]indole]-2',4(1'H)-dione and (1S,6R)-6'-Chloro-6-(3-chlorophenyl)-3-(2-methoxyphenyl)spiro[2-cyclohexene-1,3'-[3H]indole]-2',4(1'H)-dione

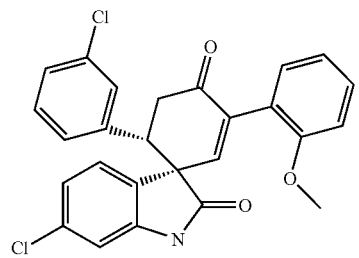

M. W. 464.4 C₂₆H₁₉Cl₂NO₃

In a manner similar to the method described in example 2 (method C, step 3), rac-(1R, 4S, 6S)-6'-chloro-6-(3-chlorophenyl)-3-(2-methoxyphenyl)-4-hydroxyspiro[2-cyclohexene-1,3'-[3H]indol]-2'(1'H)-one (60 mg, 0.13 mmol) was reacted with MnO₂ (400 mg) in CH₂Cl₂ (10 mL) were heated to reflux for 4 hrs to give rac-(1R,6S)-6'-Chloro-6-(3-chlorophenyl)-3-(2-methylphenyl)spiro[2-cyclohexene-1,3'-[3H]indole]-2',4(1'H)-dione (45.8 mg, 76.7%): HRMS (ES+) m/z Calcd for $C_{26}H_{19}Cl_2NO_3$+H [(M+H)+]: 464.0815, found: 464.0814. rac-(1R, 4S, 6S)-6'-chloro-6-(3-chlorophenyl)-3-(2-methoxyphenyl)-4-hydroxyspiro[2-cyclohexene-1,3'-[3H]indol]-2'(1'H)-one was further separated by chiral chromatography to give (1R,6S)-6'-Chloro-6-(3-chlorophenyl)-3-(2-methoxyphenyl)spiro[2-cyclohexene-1,3'-[3H]indole]-2',4(1'H)-dione and (1S,6R)-6'-Chloro-6-(3-chlorophenyl)-3-(2-methoxyphenyl)spiro[2-cyclohexene-1,3'-[3H]indole]-2',4(1'H)-dione Example 9

Preparation of rac-(1S,6S)-6'-Chloro-6-(3-chlorophenyl)-2-(2-methoxyphenyl)spiro[2-cyclohexene-1,3'-[3H]indole]-2',4(1'H)-dione

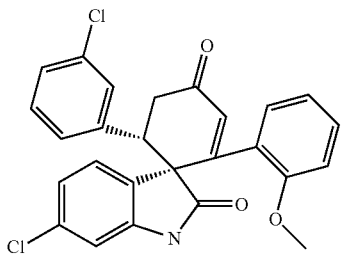

M. W. 464.4 $C_{26}H_{19}Cl_2NO_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (96.8 mg, 0.20 mmol) was reacted with 2-methoxyphenylboronic acid (60.4 mg, 0.40 mmol) in the presence of Pd(PCy$_3$)$_2$Cl$_2$ (1.4 mg, 0.005 mmol), Cs$_2$CO$_3$ (130.0 mg, 0.40 mmol) in a mixture of THF (1.6 mL) and water (0.4 mL) in a sealed tube was heated to 90° C. overnight to give rac-(1R,6S)-6'-chloro-6-(3-chlorophenyl)-3-(-2-methylphenyl) spiro[2-cyclohexene-1,3'-[3H]indole]-2',4(1'H)-dione (10.8 mg, 11.6%) and rac-(1S,6S)-6'-chloro-6-(3-chlorophenyl)-2-(2-methoxyphenyl)spiro[2-cyclohexene-1,3'-[3H]indole]-2',4(1'H)-dione (10.2 mg, 11.0%):HRMS (ES+) m/z Calcd for $C_{26}H_{19}Cl_2NO_3$ +H [(M+H)+]: 464.0815. Found: 464.0813.

Example 10

Preparation of rac-(1R, 6S)-6'-chloro-6-(3-chlorophenyl)-3-(E)-(1-propenyl)spiro[2-cyclohexene-1,3'-[3H]indole]-2',4(1'H)-dione (Compound A) and rac-(1S,6S)-6'-chloro-6-(3-chlorophenyl)-2-(E)-(1-propenyl)spiro[2-cyclohexene-1,3'-[3H]indole]-2',4(1'H)-dione (Compound B)

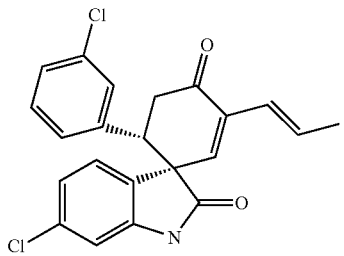

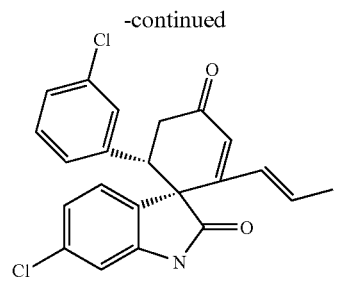

M. W. 398.3 $C_{22}H_{17}Cl_2NO_2$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (48.4 mg, 0.10 mmol) was reacted with (E)-1-prepenylboronic acid (17.2 mg, 0.20 mmol) in the presence of Pd(OAc)$_2$ (2.2 mg, 0.01 mmol), PPh$_3$ (13.1 mg, 0.05 mmol), Cs$_2$CO$_3$ (65.0 mg, 0.20 mmol) in toluene (2.0 mL) in a sealed tube was heated to 140° C. for 10 min with microwave reactor to give rac-(1R,6S)-6'-chloro-6-(3-chlorophenyl)-3-(E)-(1-propenyl)spiro[2-cyclohexene-1,3'-[3H]indole]-2',4(1'H)-dione (6.3 mg, 15.8%): HRMS (ES+) m/z Calcd for $C_{22}H_{17}Cl_2NO_2$+H [(M+H)+]: 398.0709. Found: 398.0708, and rac-(1S,6S)-6'-chloro-6-(3-chlorophenyl)-2-(E)-(1-propenyl)spiro[2-cyclohexene-1,3'-[3H]indole]-2',4(1'H)-dione (10.8 mg, 27.1%): HRMS (ES+) m/z Calcd for $C_{22}H_{17}Cl_2NO_2$+H [(M+H)+]: 398.0709 Found: 398.0707.

Example 11

Preparation of rac-(1S,6S)-6'-chloro-6-(3-chlorophenyl)-2-(4-methoxyphenyl)spiro[2-cyclohexene-1,3'-[3H]indole]-2',4(1'H)-dione and rac-(1R,6S)-6'-chloro-6-(3-chlorophenyl)-3-(4-methoxyphenyl)spiro[2-cyclohexene-1,3'-[3H]indole]-2',4(1'H)-dione

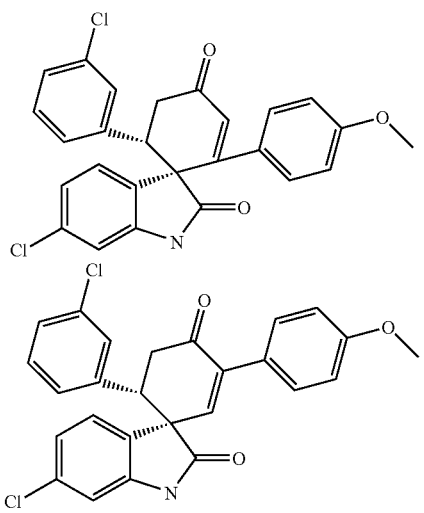

M. W. 464.4 $C_{26}H_{19}Cl_2NO_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (96.8 mg, 0.20 mmol) was reacted with 4-methoxyphenyl boronic acid (60.4 mg, 0.40 mmol) in the presence of Pd(OAc)$_2$ (2.2 mg, 0.01 mmol), PPh$_3$ (13.1 mg, 0.05 mmol), Cs$_2$CO$_3$ (130.3 mg, 0.40 mmol) in toluene (3.0 mL) in a sealed tube was heated to 160° C. for 20 min with microwave reactor to give rac-(1S,6S)-6'-chloro-6-(3-chlorophenyl)-2-(4-methoxyphenyl)spiro[2-cyclohexene-1,3'-[3H]indole]-2',4(1'H)-dione (18.8 mg, 20.3%): HRMS (ES$^+$) m/z Calcd for C$_{26}$H$_{19}$Cl$_2$NO$_3$+H [(M+H)$^+$]: 464.0815. Found: 464.0815, and rac-(1S,6S)-6'-chloro-6-(3-chlorophenyl)-3-(4-methoxyphenyl)spiro[2-cyclohexene-1,3'-[3H]indole]-2',4(1'H)-dione (12.9 mg, 13.9%): HRMS (ES$^+$) m/z Calcd for C$_{26}$H$_{19}$Cl$_2$NO$_3$+H [(M+H)$^+$]: 464.0815. Found: 464.0815

Example 12

Preparation of rac-(1S,6S)-6'-chloro-6-(3-chlorophenyl)-2-(methylethenyl)spiro[2-cyclohexene-1,3'-[3H]indole]-2',4(1'H)-dione and rac-(1R,6S)-6'-chloro-6-(3-chlorophenyl)-3-(methylethenyl)spiro[2-cyclohexene-1,3'-[3H]indole]-2',4(1'H)-dione

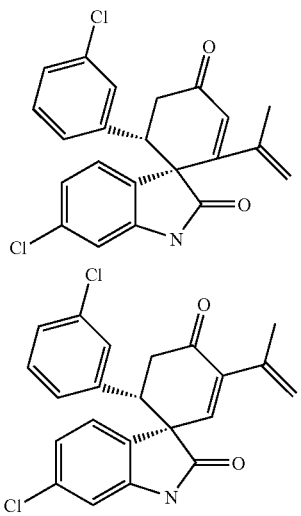

M. W. 398.3 C$_{22}$H$_{17}$Cl$_2$NO$_2$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (48.4 mg, 0.10 mmol) was reacted with 2-Isopropenyl-4,4,5,5-tetramethyl-[1,3,2]dioxaborolane (35.4 mg, 0.20 mmol) in the presence of Pd(PPh$_3$)$_4$ (5.8 mg, 0.005 mmol), Cs$_2$CO$_3$ (133.2 mg, 0.40 mmol) in a mixture of THF (3.0 mL) and water (0.3 mL) in a sealed tube was heated to 80° C. for 10 hrs to give rac-(1S,6S)-6'-chloro-6-(3-chlorophenyl)-2-(methylethenyl)spiro[2-cyclohexene-1,3'-[3H]indole]-2',4(1'H)-dione (10.8 mg, 27.1%): HRMS (ES$^+$) m/z Calcd for C$_{22}$H$_{17}$Cl$_2$NO$_2$+H [(M+H)$^+$]: 398.0709. Found: 398.07103 and rac-(1R,6S)-6'-chloro-6-(3-chlorophenyl)-3-(methylethenyl)spiro[2-cyclohexene-1,3'-[3H]indole]-2',4(1'H)-dione (6.3 mg, 15.8%): HRMS (ES$^+$) m/z Calcd for C$_{22}$H$_{17}$Cl$_2$NO$_2$+H [(M+H)$^+$]: 398.0709. Found: 398.0711.

Example 13

Preparation of rac-(1R, 4S, 6S)-6'-chloro-6-(3-chlorophenyl)-3-(1,2-dimethyl-1-propenyl)-4-hydroxyspiro[2-cyclohexene-1,3'-[3H]indol]-2'(1'H)-one

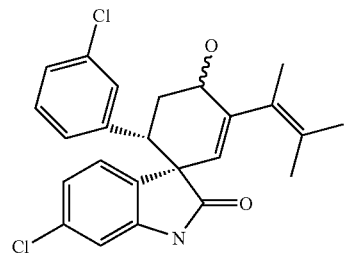

M. W. 428.4 C$_{24}$H$_{23}$Cl$_2$NO$_2$

In a manner similar to the method described in example 2 (method C, step 2), rac-(1R, 4S, 6S)-6'-chloro-6-(3-chlorophenyl)-4-hydroxy-3-iodospiro[2-cyclohexene-1,3'-[3H]indol]-2'(1'H)-one (48.6 mg, 0.10 mmol) was reacted with 1,2-dimethyl-1-propenylboronic acid (22.8 mg, 0.20 mmol) in the presence of Pd(PPh$_3$)$_4$ (5.6 mg, 0.005 mmol), Cs$_2$CO$_3$ (130.0 mg, 0.4 mmol) in a mixture of THF (1.6 mL) and water (0.4 mL) in a sealed tube was heated to 120° C. for 10 min with microwave reactor to give rac-(1R,4S,6S)-6'-chloro-6-(3-chlorophenyl)-3-(1,2-dimethyl-1-propenyl)-4-hydroxyspiro[2-cyclohexene-1,3'-[3H]indol]-2'(1'H)-one (35.5 mg, 82.9%): HRMS (ES$^+$) m/z Calcd for C$_{24}$H$_{23}$Cl$_2$NO$_2$+H [(M+H)$^+$]: 428.1179, found: 428.1179.

Example 14

Preparation of rac-(1R,6S)-6'-chloro-6-(3-chlorophenyl)-3-(1,2-dimethyl-1-propenyl)spiro[2-cyclohexene-1,3'-[3H]indole]-2',4(1'H)-dione

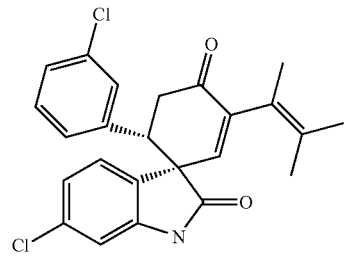

M. W. 426.4 C$_{24}$H$_{21}$Cl$_2$NO$_2$

In a manner similar to the method described in example 2 (method C, step 3), rac-(1R, 4S, 6S)-6'-chloro-6-(3-chlorophenyl)-3-(1,2-dimethyl-1-propenyl)-4-hydroxyspiro[2-cyclohexene-1,3'-[3H]indol]-2'(1'H)-one (30 mg, 0.071 mmol) was reacted with MnO$_2$ (200 mg) in CH$_2$Cl$_2$ (5 mL) were heated to 35° C. for 4 hrs to give rac-(1R,6S)-6'-chloro-6-(3-chlorophenyl)-3-(1,2-dimethyl-1-propenyl)spiro[2-cyclohexene-1,3'-[3H]indol]-2',4(1'H)-dione (19.8 mg, 66.0%): HRMS (ES$^+$) m/z Calcd for C$_{24}$H$_{21}$Cl$_2$NO$_2$+H [(M+H)$^+$]: 426.1022, found: 426.1021.

Example 15

Preparation of rac-(1S,6S)-6'-chloro-6-(3-chlorophenyl)-2-(3-methoxyphenyl)spiro[2-cyclohexene-1,3'-[3H]indole]-2',4(1'H)-dione and rac-(1R,6S)-6'-chloro-6-(3-chlorophenyl)-3-(3-methoxyphenyl)spiro[2-cyclohexene-1,3'-[3H]indole]-2',4(1'H)-dione

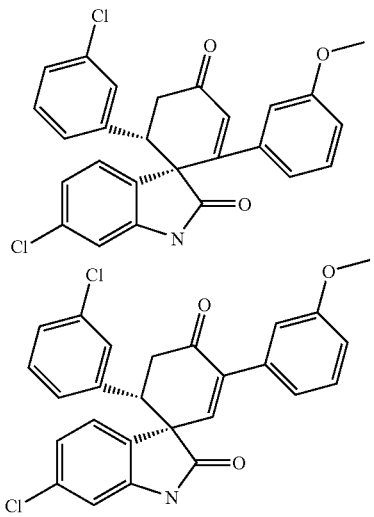

M. W. 464.4 $C_{26}H_{19}Cl_2NO_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (48.4 mg, 0.10 mmol) was reacted with 3-methoxyphenyl boronic acid (30.4 mg, 0.20 mmol) in the presence of Pd(PPh$_3$)$_4$ (9.0 mg, 0.008 mmol), Cs$_2$CO$_3$ (65.2 mg, 0.20 mmol) in a mixture of THF (1.6 mL) and water (0.4 mL) in a sealed tube was heated to 90° C. overnight to give rac-(1S,6S)-6'-chloro-6-(3-chlorophenyl)-2-(3-methoxyphenyl)spiro[2-cyclohexene-1,3'-[3H]indole]-2',4(1'H)-dione (21.3 mg, 45.7%): HRMS (ES$^+$) m/z Calcd for $C_{26}H_{19}Cl_2NO_3$+H [(M+H)$^+$]: 464.0815. Found: 464.0817, and rac-(1S,6S)-6'-chloro-6-(3-chlorophenyl)-3-(3-methoxyphenyl)spiro[2-cyclohexene-1,3'-[3H]indole]-2',4(1'H)-dione (10.9 mg, 23.4%): HRMS (ES$^+$) m/z Calcd for $C_{26}H_{19}Cl_2NO_3$+H [(M+H)$^+$]: 464.0815, Found: 464.0817

Example 16

Preparation of rac-(1S,6S)-6'-Chloro-6-(3-chlorophenyl)-2-(2-ethoxyphenyl)spiro[2-cyclohexene-1,3'-[3H]indole]-2',4(1'H)-dione and rac-(1R,6S)-6'-chloro-6-(3-chlorophenyl)-3-(2-ethoxyphenyl)spiro[2-cyclohexene-1,3'-[3H]indole]-2',4(1'H)-dione

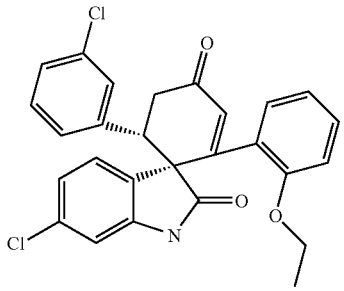

-continued

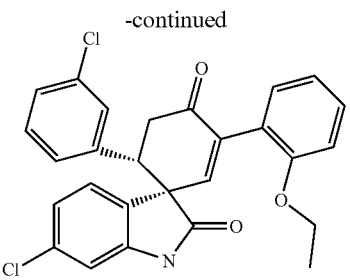

M. W. 478.4 $C_{26}H_{21}Cl_2NO_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (96.8 mg, 0.20 mmol) was reacted with 2-ethoxyphenylboronic acid (66.4 mg, 0.40 mmol) in the presence of Pd(PCy$_3$)$_2$Cl$_2$ (1.4 mg, 0.005 mmol), Cs$_2$CO$_3$ (130.0 mg, 0.40 mmol) in a mixture of 1,4-dioxane (2.0 mL) and water (1.0 mL) in a sealed tube was heated to 90° C. overnight to give rac-(1R,6S)-6'-chloro-6-(3-chlorophenyl)-2-(-2-ethylphenyl)spiro[2-cyclohexene-1,3'-[3H]indole]-2',4(1'H)-dione (12.8 mg, 13.4%): HRMS (ES$^+$) m/z Calcd for $C_{26}H_{21}Cl_2NO_3$+H [(M+H)$^+$]: 478.0971. Found 4780.970 and rac-(1S,6S)-6'-chloro-6-(3-chlorophenyl)-3-(2-ethoxyphenyl)spiro[2-cyclohexene-1,3'-[3H]indole]-2',4(1'H)-dione (13.5 mg, 14.1%): HRMS (ES$^+$) m/z Calcd for $C_{26}H_{21}Cl_2NO_3$+H [(M+H)$^+$]: 478.0971. Found: 478.0969.

Example 17

Preparation of rac-(1R,6S)-6'-chloro-6-(3-chlorophenyl)-3-(5-fluoro-2-hydroxyphenyl)spiro[2-cyclohexene-1,3'-[3H]indole]-2',4(1'H)-dione

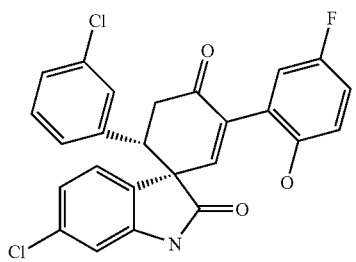

M. W. 468.3 $C_{25}H_{16}Cl_2FNO_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (242.0 mg, 0.50 mmol) was reacted with 5-fluoro-2-hydroxyphenyl boronic acid (160.7 mg, 1.0 mmol) in the presence of Pd(PPh$_3$)$_4$ (35.0 mg, 0.03 mmol), Cs$_2$CO$_3$ (325.8 mg, 1.0 mmol) in a mixture of THF (2.5 mL) and water (0.5 mL) in a sealed tube was heated to 130° C. for 10 min using a microwave reactor to give rac-(1R,6S)-6'-chloro-6-(3-chlorophenyl)-3-(5-fluoro-2-hydroxyphenyl)spiro[2-cyclohexene-1,3'-[3H]indole]-2',4(1'H)-dione (121.9 mg, 51.9%): HRMS (ES$^+$) m/z Calcd for $C_{25}H_{16}Cl_2FNO_3$+H [(M+H)$^+$]: 468.0564. Found: 468.0563.

Example 18

Preparation of rac-(1R,6S)-6'-chloro-6-(3-chlorophenyl)-3-(4-fluoro-2-hydroxyphenyl)spiro[2-cyclohexene-1,3'-[3H]indole]-2',4(1'H)-dione

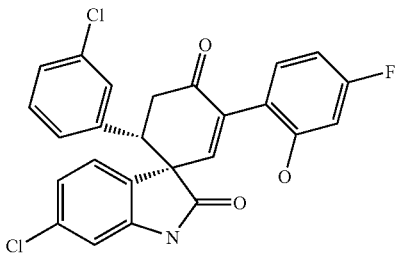

M. W. 468.3 C$_{25}$H$_{16}$Cl$_2$FNO$_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (242.0 mg, 0.50 mmol) was reacted with 4-fluoro-2-hydroxyphenyl boronic acid (160.7 mg, 1.0 mmol) in the presence of Pd(PPh$_3$)$_4$ (35.0 mg, 0.03 mmol), Cs$_2$CO$_3$ (325.8 mg, 1.0 mmol) in a mixture of THF (2.5 mL) and water (0.5 mL) in a sealed tube was heated to 130° C. for 10 min using a microwave reactor to give rac-(1R,6S)-6'-chloro-6-(3-chlorophenyl)-3-(4-fluoro-2-hydroxyphenyl)spiro[2-cyclohexene-1,3'-[3H]indole]-2',4(1'H)-dione (73.1 mg, 31.2%): HRMS (ES$^+$) m/z Calcd for C$_{25}$H$_{16}$Cl$_2$FNO$_3$+H [(M+H)$^+$]: 468.0564. Found: 468.0562.

Example 19

Preparation of rac-(1R,6S)-6'-chloro-3-(5-chloro-2-ethoxyphenyl)-6-(3-chlorophenyl)spiro[2-cyclohexene-1,3'-[3H]indole]-2',4(1'H)-dione

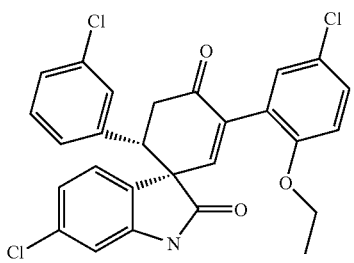

M. W. 512.8 C$_{27}$H$_{20}$Cl$_3$NO$_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 5-chloro-2-ethoxyphenyl boronic acid (48.0 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-3-(5-chloro-2-ethoxyphenyl)-6-(3-chlorophenyl)spiro[2-cyclohexene-1,3'-[3H]indole]-2',4(1'H)-dione (35.2 mg, 57.3%): HRMS (ES$^+$) m/z Calcd for C$_{27}$H$_{20}$Cl$_3$NO$_3$+H [(M+H)$^+$]: 512.0582, Found: 512.0580,

Example 20

Preparation of rac-(1R,6S)-6'-chloro-6-(3-chlorophenyl)-3-(2-phenoxyphenyl)spiro[2-cyclohexene-1,3'-[3H]indole]-2',4(1'H)-dione

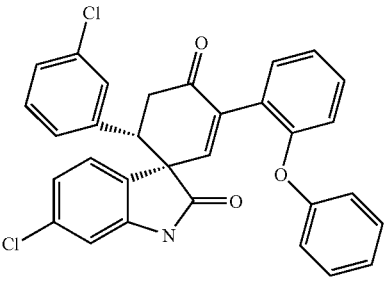

M. W. 526.4 C$_{31}$H$_{21}$Cl$_2$NO$_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 2-phenoxyphenyl boronic acid (51.3 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-(2-phenoxyphenyl)spiro[2-cyclohexene-1,3'-[3H]indole]-2',4(1'H)-dione (15.0 mg, 23.7%): HRMS (ES$^+$) m/z Calcd for C$_{31}$H$_{21}$Cl$_2$NO$_3$+H [(M+H)$^+$]: 526.0967. Found: 526.0971.

Example 21

Preparation of rac-(1R,6S)-6'-chloro-3-(4-chloro-2-ethoxyphenyl)-6-(3-chlorophenyl)spiro[2-cyclohexene-1,3'-[3H]indole]-2',4(1'H)-dione

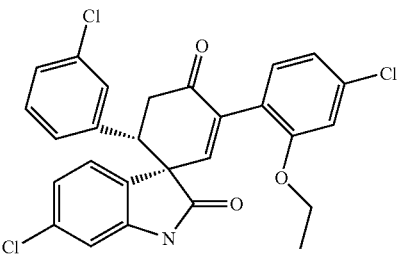

M. W. 512.8 C$_{27}$H$_{20}$Cl$_3$NO$_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 5-chloro-2-ethoxyphenyl boronic acid (48.0 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-3-(4-chloro-2-ethoxyphenyl)-6-(3-chlorophenyl)spiro[2-cyclohexene-1,3'-[3H]indole]-2',4(1'H)-dione (41.9 mg, 68.2%): HRMS (ES$^+$) m/z Calcd for $C_{27}H_{20}Cl_3NO_3$+H [(M+H)$^+$]: 512.0582, Found: 512.0578.

Example 22

Preparation of rac-(1R,6S)-6'-chloro-3-(4-chloro-2-methoxyphenyl)-6-(3-chlorophenyl)spiro[2-cyclohexene-1,3'-[3H]indole]-2',4(1'H)-dione

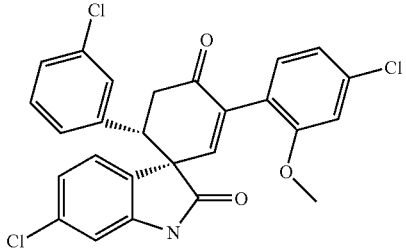

M. W. 498.8 $C_{26}H_{18}Cl_3NO_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 5-chloro-2-methoxyphenyl boronic acid (44.7 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-3-(4-chloro-2-methoxyphenyl)-6-(3-chlorophenyl)spiro[2-cyclohexene-1,3'-[3H]indole]-2',4(1'H)-dione (37.6 mg, 62.8%): HRMS (ES$^+$) m/z Calcd for $C_{26}H_{18}Cl_3NO_3$+H [(M+H)$^+$]: 498.0425, Found: 498.0425.

Example 23

Preparation of rac-(1R,6S)-6'-chloro-6-(3-chlorophenyl)-3-(2-ethoxy-5-methylphenyl)spiro[2-cyclohexene-1,3'-[3H]indole]-2',4(1'H)-dione

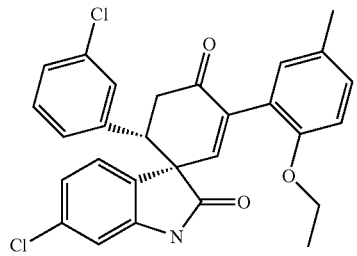

M. W. 492.4 $C_{28}H_{23}Cl_2NO_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 2-ethoxy-5-methylphenyl boronic acid (43.2 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-(2-ethoxy-5-methylphenyl)spiro[2-cyclohexene-1,3'-[3H]indole]-2',4(1'H)-dione (44.8 mg, 75.8%): HRMS (ES$^+$) m/z Calcd for $C_{26}H_{18}Cl_3NO_3$+H [(M+H)$^+$]: 492.1127 Found: 492.1128.

Example 24

Preparation of rac-(1R,6S)-6'-chloro-6-(3-chlorophenyl)-3-[2-(trifluoromethoxy)phenyl)]spiro[2-cyclohexene-1,3'-[3H]indole]-2',4(1'H)-dione

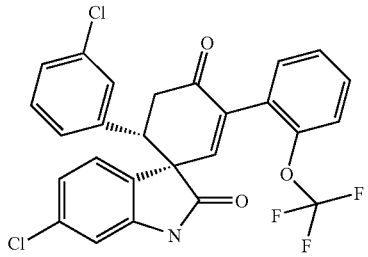

M. W. 518.3 $C_{26}H_{16}Cl_2F_3NO_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 2-trifluoromethoxy-phenyl boronic acid (49.4 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-[2-(trifluoromethoxy)phenyl]spiro[2-cyclohexene-1,3'-[3H]indole]-2',4(1'H)-dione (46.7 mg, 75.1%): HRMS (ES$^+$) m/z Calcd fr $C_{26}H_{16}Cl_2F_3NO_3$+H [(M+H)$^+$]: 518.0532. Found: 518.0532.

Example 25

Preparation of rac-(1R,6S)-6'-chloro-6-(3-chlorophenyl)-3-(3-furanyl)spiro[2-cyclohexene-1,3'-[3H]indole]-2',4(1'H)-dione

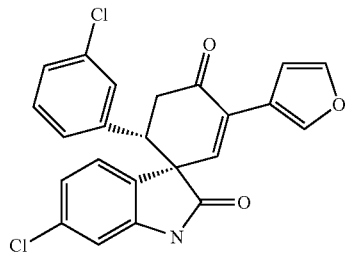

M. W. 424.3 $C_{23}H_{15}Cl_2NO_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 3-furanyl boronic acid (26.9 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-(3-furanyl)spiro[2-cyclohexene-1,3'-[3H]indole]-2',4(1'H)-dione (41.9 mg, 82.3%): HRMS (ES$^+$) m/z Calcd tor C$_{23}$H$_{15}$Cl$_2$NO$_3$+H [(M+H)$^+$]: 424.0502 Found: 424.0502.

Example 26

Preparation of rac-(1R,6S)-6'-chloro-6-(3-chlorophenyl)-3-(4-hydroxymethylphenyl)spiro[2-cyclohexene-1,3'-[3H]indole]-2',4(1'H)-dione

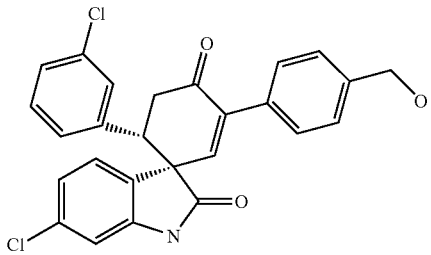

M. W. 464.4 C$_{26}$H$_{19}$Cl$_2$NO$_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 4-hydroxymethylpheny boronic acid (36.5 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-(4-hydroxymethylphenyl)spiro[2-cyclohexene-1,3'-[3H]indole]-2',4(1'H)-dione (28.3 mg, 50.8%): HRMS (ES$^+$) m/z Calcd for C$_{26}$H$_{19}$Cl$_2$NO$_3$+H [(M+H)$^+$]: 464.0815. Found: 464.0814.

Example 27

Preparation of rac-(1R,6S)-6'-chloro-6-(3-chlorophenyl)-3-(3,5-dimethyl-4-isoxazolyl)spiro[2-cyclohexene-1,3'-[3H]indole]-2',4(1'H)-dione

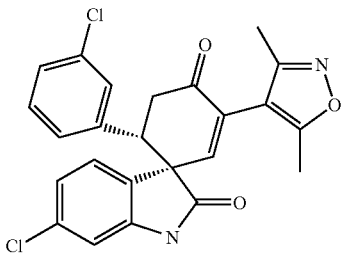

M. W. 453.3 C$_{24}$H$_{18}$Cl$_2$N$_2$O$_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 3,5-dimethylisoxazol-4-yl boronic acid (33.8 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-(3,5-dimethyl-4-isoxazolyl)spiro[2-cyclohexene-1,3'-[3H]indole]-2',4(1'H)-dione (40.2 mg, 73.9%): HRMS (ES$^+$) m/z Calcd for C$_{24}$H$_{18}$Cl$_2$N$_2$O$_3$+H [(M+H)$^+$]: 453.0767. Found: 453.0768.

Example 28

Preparation of rac-(1R,6S)-6'-chloro-6-(3-chlorophenyl)-3-(1-cyclohexenyl)spiro[2-cyclohexene-1,3'-[3H]indole]-2',4(1'H)-dione

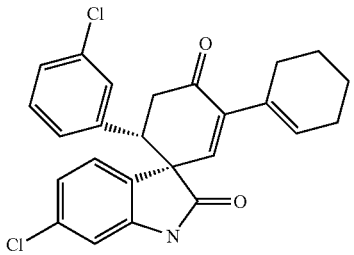

M. W. 438.4 C$_{25}$H$_{21}$Cl$_2$NO$_2$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 1-cyclohexenyl boronic acid (30.2 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-(1-cyclohexenyl)spiro[2-cyclohexene-1,3'-[3H]indole]-2',4(1'H)-dione (33.2 mg, 61.0%): HRMS (ES$^+$) m/z Calcd for C$_{25}$H$_{21}$Cl$_2$NO$_2$+H [(M+H)$^+$]: 438.1022. Found: 438.1024.

Example 29

Preparation of rac-(1R,6S)-6'-chloro-6-(3-chlorophenyl)-3-(2-hydroxymethylphenyl)spiro[2-cyclohexene-1,3'-[3H]indole]-2',4(1'H)-dione

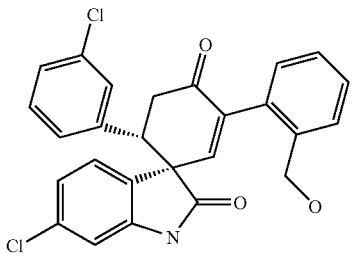

M. W. 464.4 C$_{26}$H$_{19}$Cl$_2$NO$_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (65.0 mg, 0.12 mmol) was reacted with 2-hydroxymethylpheny boronic acid (36.5 mg, 0.24 mmol) in the presence of Pd(PPh$_3$)$_4$ (8.0 mg, 0.007 mmol), Cs$_2$CO$_3$ (78.0 mg, 0.24 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-(2-hydroxymethylphenyl)spiro[2-cyclohexene-1,3'-[3H]indole]-2',4(1'H)-dione (20.8 mg, 37.3%): HRMS (ES$^+$) m/z Calcd for C$_{26}$H$_{19}$Cl$_2$NO$_3$−H [(M−H)$^+$]: 462.0669, Found: 462.0667.

Example 30

Preparation of rac-(1R,6S)-6'-chloro-6-(3-chlorophenyl)-3-(3-hydroxymethylphenyl)spiro[2-cyclohexene-1,3'-[3H]indole]-2',4(1'H)-dione

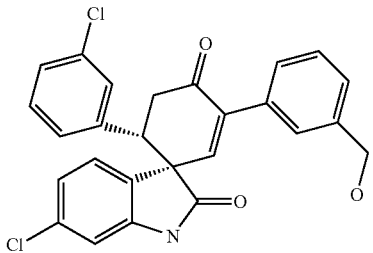

M. W. 464.4 C$_{26}$H$_{19}$Cl$_2$NO$_3$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (52.8 mg, 0.10 mmol) was reacted with 3-hydroxymethylpheny boronic acid (30.4 mg, 0.20 mmol) in the presence of Pd(PPh$_3$)$_4$ (8.0 mg, 0.007 mmol), Cs$_2$CO$_3$ (65.2 mg, 0.20 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-(3-hydroxymethylphenyl)spiro[2-cyclohexene-1,3'-[3H]indole]-2',4(1'H)-dione (24.8 mg, 53.4%): HRMS (ES$^+$) m/z Calcd tor C$_{26}$H$_{19}$Cl$_2$NO$_3$−H [(M−H)$^+$]: 462.0669. Found 462.0668.

Example 31

Preparation of rac-(1S,6S)-6'-chloro-6-(3-chlorophenyl)-3-[3-(methoxycarbonyl)phenyl]spiro[2-cyclohexene-1,3'-[3H]indole]-2',4(1'H)-dione

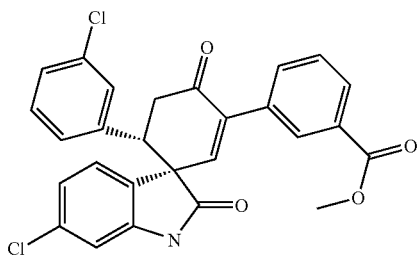

M. W. 492.4 C$_{27}$H$_{19}$Cl$_2$NO$_4$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (52.8 mg, 0.10 mmol) was reacted with 3-(methoxycarbonyl)pheny boronic acid (36.0 mg, 0.20 mmol) in the presence of Pd(PPh$_3$)$_4$ (8.0 mg, 0.007 mmol), Cs$_2$CO$_3$ (65.2 mg, 0.20 mmol) in a mixture of THF (2.5 mL) and water (0.5 mL) in a sealed tube was heated to 120° C. for 15 min using a microwave reactor followed by treatment with pTsOH to give rac-(1S,6S)-6'-chloro-6-(3-chlorophenyl)-3-[3-(methoxycarbonyl)phenyl]spiro[2-cyclohexene-1,3'-[3H]indole]-2',4(1'H)-dione (25.1 mg, 51.0%): HRMS (ES$^+$) m/z Calcd for C$_{26}$H$_{19}$Cl$_2$NO$_3$+H [(M+H)$^+$]: 492.0764. Found: 492.0763.

Example 32

Preparation of rac-(1S,6S)-6'-chloro-6-(3-chlorophenyl)-3-[4-(methoxycarbonyl)phenyl]spiro[2-cyclohexene-1,3'-[3H]indole]-2',4(1'H)-dione

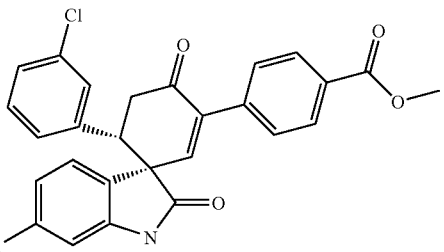

M. W. 492.4 C$_{27}$H$_{19}$Cl$_2$NO$_4$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (52.8 mg, 0.10 mmol) was reacted with 4-(methoxycarbonyl)pheny boronic acid (36.0 mg, 0.20 mmol) in the presence of Pd(PPh$_3$)$_4$ (8.0 mg, 0.007 mmol), Cs$_2$CO$_3$ (65.2 mg, 0.20 mmol) in a mixture of THF (2.5 mL) and water (0.5 mL) in a sealed tube was heated to 120° C. for 15 min using a microwave reactor followed by treatment with pTsOH to give rac-(1S,6S)-6'-chloro-6-(3-chlorophenyl)-3-[4-(methoxycarbonyl)phenyl]spiro[2-cyclohexene-1,3'-[3H]indole]-2',4(1'H)-dione (29.6 mg, 60.2%): HRMS (ES$^+$) m/z Calcd for C$_{26}$H$_{19}$Cl$_2$NO$_3$+H [(M+H)$^+$]: 492.0764. Found: 492.0761.

Example 33

Preparation of rac-(1R,6S)-6'-chloro-3-(3-carboxyphenyl)-6-(3-chlorophenyl)spiro[2-cyclohexene-1,3'-[3H]indole]-2',4(1'H)-dione

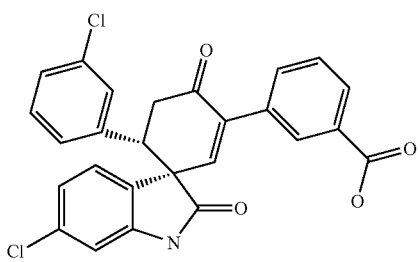

M. W. 478.3 C$_{26}$H$_{17}$Cl$_2$NO$_4$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (52.8 mg, 0.10 mmol) was reacted with 3-carboxyphenyl boronic acid (50.0 mg, 0.30 mmol) in the presence of Pd(PPh$_3$)$_4$ (8.0 mg, 0.007 mmol), Cs$_2$CO$_3$ (98.0 mg, 0.30 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-3-(3-carboxyphenyl)-6-(3-chlorophenyl)spiro[2-cyclohexene-1, 3'-[3H]indole]-2',4(1'H)-dione (11.3 mg, 23.0%): HRMS (ES$^+$) m/z Calcd for C$_{26}$H$_{17}$Cl$_2$NO$_4$+H [(M+H)$^+$]: 478.0608. Found: 478.0605.

Example 34

Preparation of rac-(1R,6S)-6'-chloro-6-(3-chlorophenyl)-3-(3-cyanophenyl)spiro[2-cyclohexene-1,3'-[3H]indole]-2',4(1'H)-dione

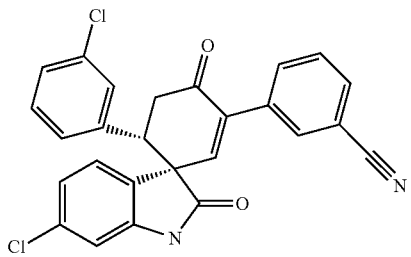

M. W. 459.3 C$_{26}$H$_{16}$Cl$_2$N$_2$O$_2$

In a manner similar to the method described in example 2 (method B, step 2 & 3), rac-(4'R,5'S)-6"-chloro-5'-(3-chlorophenyl)-2'-iododispiro[1,3-dioxolane-2,1'-[2]cyclohexene-4',3"-[3H]indol]-2"(1"H)-one (example 3) (52.8 mg, 0.10 mmol) was reacted with 3-cyanoyphenyl boronic acid (44.1 mg, 0.30 mmol) in the presence of Pd(PPh$_3$)$_4$ (8.0 mg, 0.007 mmol), Cs$_2$CO$_3$ (98.0 mg, 0.30 mmol) in a mixture of THF (2.5 mL) and water (0.5 mL) in a sealed tube was heated to 120° C. for 15 min using a microwave reactor followed by treatment with pTsOH to give rac-(1R,6S)-6'-chloro-6-(3-chlorophenyl)-3-(3-cyanophenyl)spiro[2-cyclohexene-1,3'-[3H]indole]-2',4(1'H)-dione (29.5 mg, 64.3%): HRMS (ES$^+$) m/z Calcd for C$_{26}$H$_{17}$Cl$_2$NO$_4$+H [(M+H)$^+$]: 459.0662. Found: 459.0660.

Example 35

Preparation of rac-(1R,6S)-6'-chloro-6-(3-chlorophenyl)-2-(3-propoxyphenyl)spiro[2-cyclohexene-1,3'-[3H]indole]-2',4(1'H)-dione & rac-(1R,6S)-6'-chloro-6-(3-chlorophenyl)-3-(3-propoxyphenyl)spiro[2-cyclohexene-1,3'-[3H]indole]-2',4(1'H)-dione

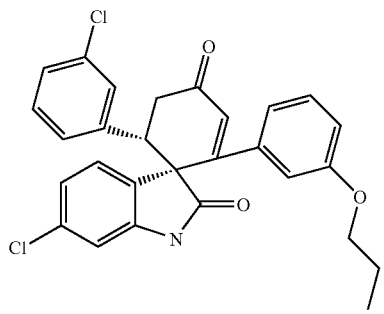

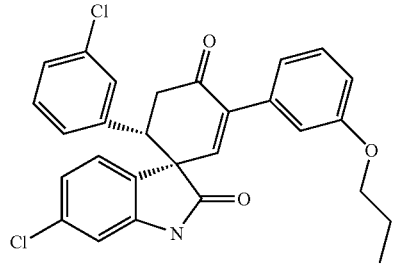

M. W. 492.4 C$_{28}$H$_{23}$Cl$_2$NO$_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (48.4 mg, 0.10 mmol) was reacted with 3-propoxyphenylboronic acid (36.0 mg, 0.20 mmol) in the presence of Pd(PPh$_3$)$_4$ (8.0 mg, 0.007 mmol), Cs$_2$CO$_3$ (98.0 mg, 0.30 mmol) in a mixture of THF (2.5 mL) and water (0.5 mL) in a sealed tube was heated to 120° C. for 15 min with microwave reactor to give rac-(1R,6S)-6'-chloro-6-(3-chlorophenyl)-2-(3-propoxyphenyl)spiro[2-cyclohexene-1,3'-[3H]indole]-2',4(1'H)-dione (11.5 mg, 23.4%): HRMS (ES$^+$) m/z Calcd for C$_{28}$H$_{23}$Cl$_2$NO$_3$+H [(M+H)$^+$]: 492.1128. Found: 492.1127, and rac-(1R,6S)-6'-chloro-6-(3-chlorophenyl)-3-(3-propoxyphenyl)spiro[2-cyclohexene-1,3'-[3H]indole]-2',4(1'H)-dione (12.8 mg, 26.0%): HRMS (ES$^+$) m/z Calcd for C$_{28}$H$_{23}$Cl$_2$NO$_3$+H [(M+H)$^+$]: 492.1128. Found: 492.1130.

Example 36

Preparation of rac-(1R,6S)-6'-chloro-6-(3-chlorophenyl)-3-(3-methyl-5-t-butylphenyl)spiro[2-cyclohexene-1,3'-[3H]indole]-2',4(1'H)-dione

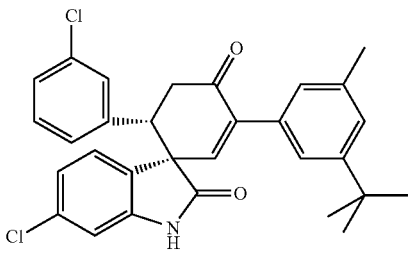

M. W. 504.454 C$_{30}$H$_{27}$Cl$_2$NO$_2$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 3-methyl-5-t-butylphenyl boronic acid (79.5 mg, 0.41 mmol) in the presence of Pd(PPh$_3$)$_4$ (19.0 mg, 0.015 mmol), K$_2$CO$_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave rac-(1R,6S)-6'-chloro-6-(3-chlorophenyl)-3-(3-methyl-5-t-butylphenyl)spiro[2-cyclohexene-1,3'-[3H]indole]-2',4

(1'H)-dione as an white powder (17.0 mg, 16.4%). HRMS (ES⁺) m/z Calcd for $C_{30}H_{27}Cl_2NO_2$+H [(M+H)⁺]: 504.1492. Found: 504.1492

Example 37

Preparation of rac-(1R,6S)-6'-chloro-6-(3-chlorophenyl)-3-(2,4,6-trimethylphenyl)spiro[2-cyclohexene-1,3'-[3H]indole]-2',4(1'H)-dione

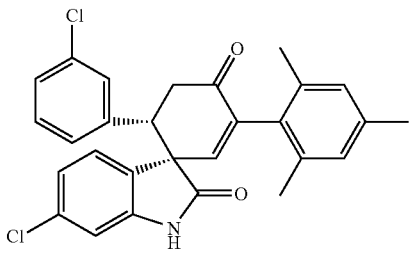

M. W. 476.401 $C_{28}H_{23}Cl_2NO_2$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 2,4,6-trimethylphenyl boronic acid (67.9 mg, 0.41 mmol) in the presence of Pd(PPh₃)₄ (19.0 mg, 0.015 mmol), $K_2CO_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave rac-(1R,6S)-6'-chloro-6-(3-chlorophenyl)-3-(2,4,6-trimethylphenyl)spiro[2-cyclohexene-1,3'-[3H]indole]-2',4(1'H)-dione as an off-white powder (6.0 mg, 6.1%). HRMS (ES⁺) m/z Calcd for $C_{28}H_{23}Cl_2NO_2$+H [(M+H)⁺]: 476.1179. Found: 476.1179

Example 38

Preparation of rac-(1R,6S)-6'-chloro-6-(3-chlorophenyl)-3-(4-t-butylphenyl)spiro[2-cyclohexene-1,3'-[3H]indole]-2',4(1'H)-dione

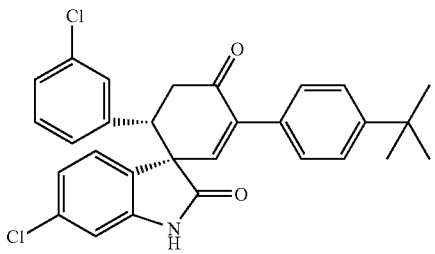

M. W. 490.427 $C_{29}H_{25}Cl_2NO_2$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 4-t-butylphenyl boronic acid (73.7 mg, 0.41 mmol) in the presence of Pd(PPh₃)₄ (19.0 mg, 0.015 mmol), $K_2CO_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave rac-(1R,6S)-6'-chloro-6-(3-chlorophenyl)-3-(4-t-butylphenyl)spiro[2-cyclohexene-1,3'-[3H]indole]-2',4(1'H)-dione as an off-white powder (3.0 mg, 3.0%). HRMS (ES⁺) m/z Calcd for $C_{29}H_{25}Cl_2NO_2$+H [(M+H)⁺]: 490.1335. Found: 490.1334

Example 39

Preparation of rac-(1R,6S)-6'-chloro-6-(3-chlorophenyl)-2-(2-methoxy-3-pyridyl)spiro[2-cyclohexene-1,3'-[3H]indole]-2',4(1'H)-dione and rac-(1R,6S)-6'-chloro-6-(3-chlorophenyl)-3-(2-methoxy-3-pyridyl)spiro[2-cyclohexene-1,3'-[3H]indole]-2',4(1'H)-dione

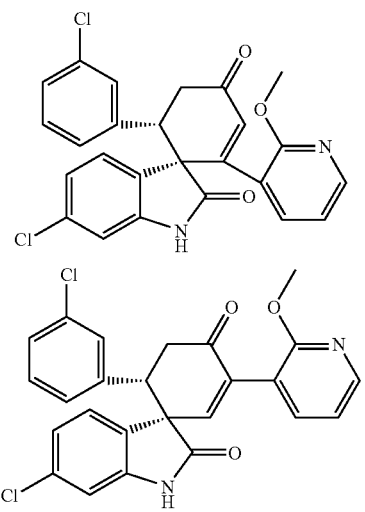

M. W. 465.334 $C_{25}H_{18}Cl_2N_2O_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 2-methoxypyridine-3-boronic acid (63.3 mg, 0.41 mmol) in the presence of Pd(PPh₃)₄ (19.0 mg, 0.015 mmol), $K_2CO_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave two products; rac-(1R,6S)-6'-chloro-6-(3-chlorophenyl)-2-(2-methoxy-3-pyridyl)spiro[2-cyclohexene-1,3'-[3H]indole]-2',4(1'H)-dione as light yellow powder (30.0 mg, 31.3%) HRMS (ES⁺) m/z Calcd for $C_{25}H_{18}Cl_2N_2O_3$+H [(M+H)⁺]: 465.0767. Found 465.0767 and rac-(1R,6S)-6'-chloro-6-(3-chlorophenyl)-3-(2-methoxy-3-pyridyl)spiro[2-cyclohexene-1,3'-[3H]indole]-2',4(1'H)-dione as an off-white powder (12.0 mg, 12.5%). HRMS (ES⁺) m/z Calcd for $C_{25}H_{18}Cl_2N_2O_3$+H [(M+H)⁺]: 465.0767. Found: 465.0768

Example 40

Preparation of rac-(1R,6S)-6'-chloro-6-(3-chlorophenyl)-3-(3-BOC-aminophenyl)spiro[2-cyclohexene-1,3'-[3H]indole]-2',4(1'H)-dione

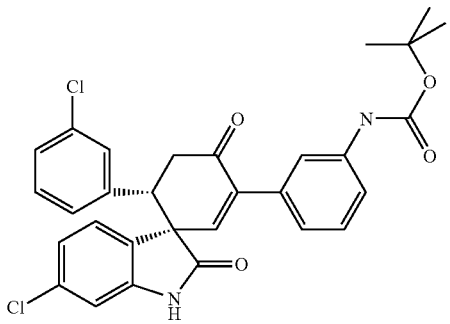

M. W. 549.451 $C_{30}H_{26}Cl_2N_2O_4$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 3-BOCaminophenyl boronic acid (62.0 mg, 0.28 mmol) in the presence of Pd(PPh$_3$)$_4$ (19.0 mg, 0.015 mmol), K$_2$CO$_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave rac-(1R,6S)-6'-chloro-6-(3-chlorophenyl)-3-(3-BOC-aminophenyl)spiro[2-cyclohexene-1,3'-[3H]indole]-2',4(1'H)-dione as an off-white powder (12.0 mg, 10.6%). HRMS (ES$^+$) m/z Calcd for $C_{30}H_{26}Cl_2N_2O_4$+H [(M+Na)$^+$]: 571.1162. Found: 571.1164

Example 41

Preparation of rac-(1R,6S)-6'-chloro-6-(3-chlorophenyl)-2-(2,6-dihydro-2H-BOC-pyridyl)spiro[2-cyclohexene-1,3'-[3H]indole]-2',4(1'H)-dione and rac-(1R,6S)-6'-chloro-6-(3-chlorophenyl)-3-(2,6-dihydro-2H-BOC-pyridyl)spiro[2-cyclohexene-1,3'-[3H]indole]-2',4(1'H)-dione

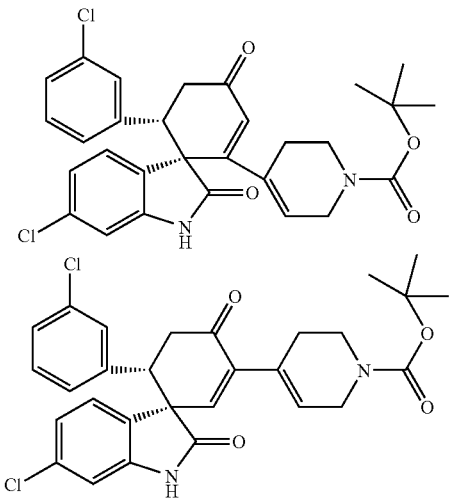

M. W. 539.456 $C_{29}H_{28}Cl_2N_2O_4$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 2,6-dihydro-2H-BOC-pyridyl boronic ester (128.0 mg, 0.41 mmol) in the presence of Pd(PPh$_3$)$_4$ (19.0 mg, 0.015 mmol), K$_2$CO$_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave two products; rac-(1R,6S)-6'-chloro-6-(3-chlorophenyl)-2-(2,6-dihydro-2H-BOC-pyridyl)spiro[2-cyclohexene-1,3'-[3H]indole]-2',4(1'H)-dione as an off white powder (12.0 mg, 10.8%) HRMS (ES$^+$) m/z Calcd for $C_{29}H_{28}Cl_2N_2O_4$+H [(M+Na)$^+$]: 561.1318. Found: 561.1319 and rac-(1R,6S)-6'-chloro-6-(3-chlorophenyl)-3-(2,6-dihydro-2H-BOC-pyridyl)spiro[2-cyclohexene-1,3'-1,3'-[3H]indole]-2',4(1'H)-dione as an off-white powder (15.0 mg, 13.5%). HRMS (ES$^+$) m/z Calcd for $C_{29}H_{28}Cl_2N_2O_4$+H [(M+Na)$^+$]: 561.1319. Found: 561.1318

Example 42

Preparation of rac-(1R,6S)-6'-chloro-6-(3-chlorophenyl)-3-(2-formylphenyl)spiro[2-cyclohexene-1,3'-[3H]indole]-2',4(1'H)-dione

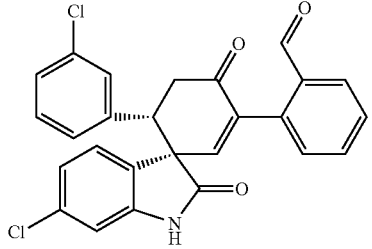

M. W. 462.33 $C_{26}H_{17}Cl_2NO_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 2-formylphenyl boronic acid (62.1 mg, 0.41 mmol) in the presence of Pd(PPh$_3$)$_4$ (19.0 mg, 0.015 mmol), K$_2$CO$_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave rac-(1R,6S)-6'-chloro-6-(3-chlorophenyl)-3-(2-formylphenyl)spiro[2-cyclohexene-1,3'-[3H]indole]-2',4(1'H)-dione as a colorless powder (13.5 mg, 14.2%). HRMS (ES$^+$) m/z Calcd for $C_{26}H_{17}Cl_2NO_3$+H [(M+H)$^+$]: #. Found: #

Example 43

Preparation of rac-(1R,6S)-6'-chloro-6-(3-chlorophenyl)-3-(3,5-bistrifluoromethylphenyl)spiro[2-cyclohexene-1,3'-[3H]indole]-2',4(1'H)-dione

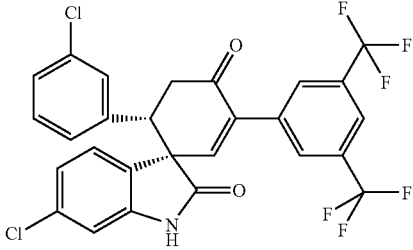

M. W. 570.315 $C_{27}H_{15}Cl_2F_6NO_2$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 3,5-bistrifluorophenyl boronic acid (106.7 mg, 0.41 mmol) in the presence of Pd(PPh$_3$)$_4$ (19.0 mg, 0.015 mmol), K$_2$CO$_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave rac-(1R,6S)-6'-chloro-6-(3-chlorophenyl)-3-(3,5-bistrifluoromethylphenyl) spiro[2-cyclohexene-1,3'-[3H]indole]-2',4(1'H)-dione as a colorless powder (5.0 mg, 4.3%). HRMS (ES$^+$) m/z Calcd for C$_{27}$H$_{15}$Cl$_2$F$_6$NO$_2$ +H [(M+H)$^+$]: 568.0311. Found: 568.0309

Example 44

Preparation of rac-(1R,6S)-6'-chloro-6-(3-chlorophenyl)-2-(2-ethylenephenyl)spiro[2-cyclohexene-1,3'-[3H]indole]-2',4(1'H)-dione (Compound A) and rac-(1R,6S)-6'-chloro-6-(3-chlorophenyl)-3-(2-ethylenephenyl)spiro[2-cyclohexene-1,3'-[3H]indole]-2',4(1'H)-dione (Compound B)

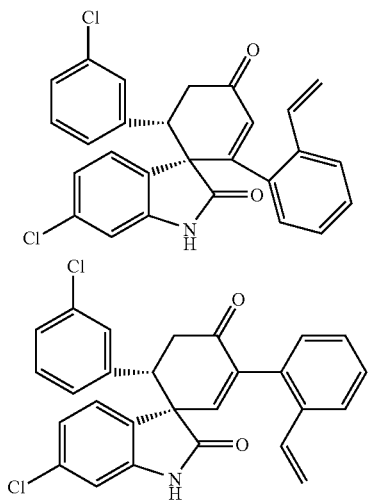

M. W. 460.358 C$_{27}$H$_{19}$Cl$_2$NO$_2$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 2-vinylbenzyl boronic acid (61.3 mg, 0.41 mmol) in the presence of Pd(PPh$_3$)$_4$ (19.0 mg, 0.015 mmol), K$_2$CO$_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave two products; rac-(1R,6S)-6'-chloro-6-(3-chlorophenyl)-2-(2-ethylenephenyl)spiro[2-cyclohexene-1,3'-[3H]indole]-2',4(1'H)-dione as an off white powder (16.0 mg, 16.9%) HRMS (ES$^+$) m/z eacd for C$_{27}$H$_{19}$Cl$_2$NO$_2$+H [(M+H)$^+$]: #. Found: # and rac-(1R,6S)-6'-chloro-6-(3-chlorophenyl)-3-(2-ethylenephenyl)spiro[2-cyclohexene-1,3'-[3H]indole]-2',4(1'H)-dione as a colorless powder (13.1 mg, 13.8%). HRMS (ES$^+$) m/z Calcd for C$_{27}$H$_{19}$Cl$_2$NO$_2$+H [(M+)$^+$]: 460.0866. Found: 460.0865

Example 45

Preparation of rac-(1R,6S)-6'-chloro-6-(3-chlorophenyl)-2-(3-methylthiophenyl)spiro[2-cyclohexene-1,3'-[3H]indole]-2',4(1'H)-dione and rac-(1R,6S)-6'-chloro-6-(3-chlorophenyl)-3-(3-methylthiophenyl)spiro[2-cyclohexene-1,3'-[3H]indole]-2',4(1'H)-dione

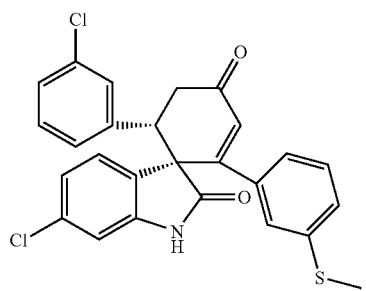

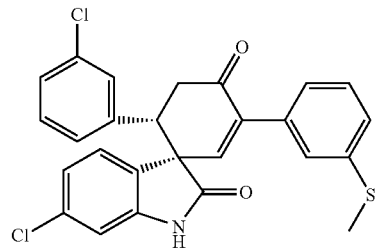

M. W. 480.413 C$_{26}$H$_{19}$Cl$_2$NO$_2$S

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 3-methylthiophenyl boronic acid (69.6 mg, 0.41 mmol) in the presence of Pd(PPh$_3$)$_4$ (19.0 mg, 0.015 mmol), K$_2$CO$_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave two products rac-(1R,6S)-6'-chloro-6-(3-chlorophenyl)-2-(3-methylthiophenyl)spiro[2-cyclohexene-1,3'-[3H]indole]-2',4(1'H)-dione as an off white powder (24.3 mg, 24.6%) HRMS (ES$^+$) m/z Calcd for C$_{27}$H$_{19}$Cl$_2$NO$_2$+H [(M+H)$^+$]: #. Found: # and rac-(1R,6S)-6'-chloro-6-(3-chlorophenyl)-3-(3-methylthiophenyl)spiro[2-cyclohexene-1,3'-[3H]indole]-2',4(1'H)-dione as a colorless powder (22.4 mg, 22.6%). HRMS (ES) m/z Calcd for C$_{27}$H$_{19}$Cl$_2$NO$_2$+H [(M+)$^+$]: 480.0587. Found: 480.0588

Example 46

Preparation of rac-(1R,6S)-6'-chloro-6-(3-chlorophenyl)-2-(3-dimethylacetamidophenyl)spiro[2-cyclohexene-1,3'-[3H]indole]-2',4(1'H)-dione and rac-(1R,6S)-6'-chloro-6-(3-chlorophenyl)-3-(3-3-dimethylacetamido phenyl)spiro[2-cyclohexene-1,3'-[3H]indole]-2',4(1'H)-dione

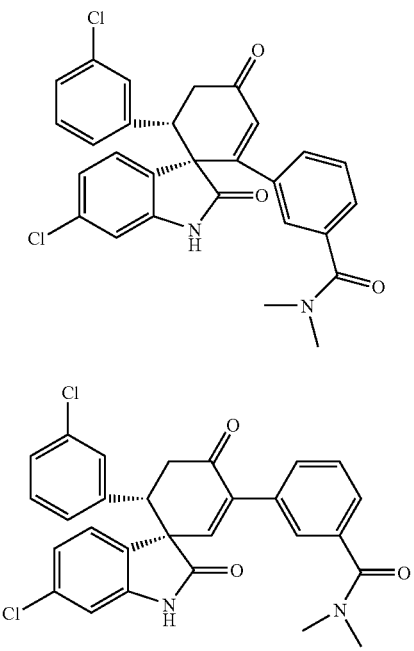

M. W. 505.399 $C_{28}H_{22}Cl_2N_2O_3$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 3-dimethylacetamidobenzyl boronic acid (79.9 mg, 0.41 mmol) in the presence of Pd(PPh$_3$)$_4$ (19.0 mg, 0.015 mmol), K$_2$CO$_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave two products rac-(1R,6S)-6'-chloro-6-(3-chlorophenyl)-2-(3-dimethylacetamidophenyl)spiro[2-cyclohexene-1,3'-[3H]indole]-2',4(1'H)-dione [RO5289881-000-001] as an off white powder (21.0 mg, 20.2%) HRMS (ES$^+$) m/z Calcd for $C_{28}H_{22}Cl_2N_2O_3$+H [(M+H)$^+$]: #. Found: # and rac-(1R,6S)-6'-chloro-6-(3-chlorophenyl)-3-(3-dimethylacetamidophenyl)spiro[2-cyclohexene-1,3'-[3H]indole]-2',4(1'H)-dione as an off-white powder (18.0 mg, 17.3%). HRMS (ES$^+$) m/z Calcd for $C_{28}H_{22}Cl_2N_2O_3$+H [(M+)$^+$]: 505.1080. Found: 505.1082

Example 47

Preparation of rac-(1R,6S)-6'-chloro-6-(3-chlorophenyl)-3-(3,4-dimethylphenyl)spiro[2-cyclohexene-1,3'-[3H]indole]-2',4(1'H)-dione

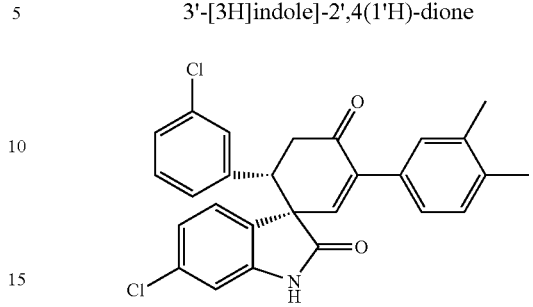

M. W. 462.38 $C_{27}H_{21}Cl_2NO_2$

In a manner similar to the method described in example 2 (method A), rac-(1R,6S)-6'-chloro-6-(3-chlorophenyl)-3-iodospiro[2-cyclohexene-1,3'-[3H]indole]-2',4(1'H)-dione (100.0 mg, 0.21 mmol) was reacted with 3,4-dimethylphenyl boronic acid (62.1 mg, 0.41 mmol) in the presence of Pd(PPh$_3$)$_4$ (19.0 mg, 0.015 mmol), K$_2$CO$_3$ (1.0 mL, 2.0 mmol, 2M) and THF (4.0 mL) in a sealed tube was heated to 110° C. for 14 hrs. Organic layer separated and solvent evaporated under vacuum. Purification with flash chromatography gave rac-(1R,6S)-6'-chloro-6-(3-chlorophenyl)-3-(3,4-dimethylphenyl)spiro[2-cyclohexene-1,3'-[3H]indole]-2',4(1'H)-dione as an off-white powder (15.0 mg, 15.7%). HRMS (ES$^+$) m/z Calcd for $C_{27}H_{21}Cl_2NO_2$+H [(M+H)$^+$]: 461.2296. Found: 461.2295

Example 48

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.), Binding of GST-MDM2 protein and p53-peptide (biotinylated on its N-terminal end) is registered by the FRET (fluorescence resonance energy transfer) between Europium (Eu)-labeled ant-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

| Example No. | IC$_{50}$ (μM, 0.02% BSA) |
| --- | --- |
| 5 | 1.60 |
| 10 (Compound B) | 5.90 |
| 17 | 1.66 |
| 18 | 2.99 |
| 44 (Compound A) | 1.39 |

What is claimed:

1. A compound of the formula

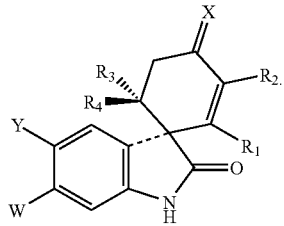

wherein

X is oxygen or hydrogen/hydroxy,

W is selected from the group consisting of hydrogen, halogen, cyano, nitro, ethynyl and cyclopropyl, Y is hydrogen or fluorine, $R_1$ is hydrogen, $R_2$ is selected from the group consisting of lower alkoxyl, lower alkenyl, lower alkynyl, aryl, substituted arly, heteroaryl, substituted heteroaryl, heterocycle, substituted heterocycle, cycloalkyl, substituted cycloalkyl, cycloalkenyl, and substituted cycloalkenyl, $R_3$ and $R_4$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl and substituted cycloalkenyl, with the proviso that one of $R_3/R_4$ is hydrogen and the other is not hydrogen, or a pharmaceutically acceptable salt or ester thereof.

2. The compound of claim 1 wherein

W is halogen

X is oxygen,

Y is hydrogen, $R_1$ is hydrogen, $R_4$ is hydrogen and $R_2$ and $R_3$ are selected from the group consisting of lower alkoxyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl.

3. The compound of claim 2 wherein

W is chlorine

X is oxygen,

Y is hydrogen, $R_1$ is hydrogen, $R_4$ is hydrogen, $R_3$ is a meta-halogen substituted phenyl with or without further substitution and $R_2$ is selected from the group consisting of lower alkenyl, aryl, and substituted aryl.

4. A compound selected from the group consisting of rac-(1R,6S)-3-bromo-6'-chloro-6-(3-chlorophenyl)spiro[2-cyclohexene-1,3'-[3H]indole]-2',4(1'H)-dione, rac-(1R,6S)-6'-chloro-6-(3-chlorophenyl)3-iodospiro[2-cyclohexene-1,3'-[3H]indole]-2',4(1'H)-dione, rac-(1R, 4S, 6S)-6'-chloro-6-(3-chlorophenyl)-4-hydroxy-3-iodospiro[2-cyclohexene-1,3'-[3H]indol]-2'(1'H)-one, rac-(1R, 4S, 6S)-6'-chloro-6-(3-chlorophenyl)-3-(5-fluoro-2-methylphenyl)-4-hydroxyspiro[2-cyclohexene-1,3'-[3H]indol]-2'(1'H)-one, rac-(1R, 6S)-6'-chloro-6-(3-chlorophenyl)-3-(E)-(1-propenyl)spiro[2-cyclohexene-1,3'-[3H]indole]-2',4(1'H)-dione, rac-(1S,6S)-6'-chloro-6-(3-chlorophenyl)-2-(E)-(1-propenyl)spiro[2-cyclohexene-1,3'-[3H]indole]-2',4(1'H)-dione, rac-(1S,6S)-6'-chloro-6-(3-chlorophenyl)-2-(methylethenyl)spiro[2-cyclohexene-1,3'-[3H]indole]-2',4(1'H)-dione, rac-(1R,6S)-6'-chloro-6-(3-chlorophenyl)-3-(methylethenyl)spiro[2-cyclohexene-1,3'-[3H]indole]-2',4(1'H)-dione, rac-(1R, 4S, 6S)-6'-chloro-6-(3-chlorophenyl)-3-(1,2-dimethyl-1-propenyl)-4-hydroxyspiro[2-cyclohexene-1,3'-[3H]indol]-2'(1'H)-one and rac-(1R,6S)-6'-chloro-6-(3-chlorophenyl)-3-(1,2-dimethyl-1-propenyl)spiro[2-cyclohexene-1,3'-[3H]indole]-2',4(1'H)-dione.

5. A compound selected from the group consisting of rac-(1S,6S)-6'-chloro-6-(3-chlorophenyl)-2-(3-methoxyphenyl)spiro[2-cyclohexene-1,3'-[3H]indole]-2',4(1'H)-dione, rac-(1R,6S)-6'-chloro-6-(3-chlorophenyl)-3-(3-methoxyphenyl)spiro[2-cyclohexene-1,3'-[3H]indole]-2',4(1'H)-dione, rac-(1S,6S)-6'-chloro-6-(3-chlorophenyl)-2-(2-ethoxyphenyl)spiro[2-cyclohexene-1,3'-[3H]indole]-2',4(1'H)-dione, rac-(1R,6S)-6'-chloro-6-(3-chlorophenyl)-3-(2-ethoxyphenyl)spiro[2-cyclohexene-1,3'-[3H]indole]-2',4(1'H)-dione, rac-(1R, 4S, 6S)-6'-chloro-6-(3-chlorophenyl)-3-(2-methoxyphenyl)-4-hydroxyspiro[2-cyclohexene-1,3'-[3H]indol]-2'(1'H)-one, rac-(1R,6S)-6'-chloro-6-(3-chlorophenyl)-3-(2-methoxyphenyl)spiro[2-cyclohexene-1,3'-[3H]indole]-2',4(1'H)-dione, rac-(1S,6S)-6'-chloro-6-(3-chlorophenyl)-2-(2-methoxyphenyl)spiro[2-cyclohexene-1,3'-[3H]indole]-2',4(1'H)-dione, rac-(1S,6S)-6'-chloro-6-(3-chlorophenyl)-2-(4-methoxyphenyl)spiro[2-cyclohexene-1,3'-[3H]indole]-2',4(1'H)-dione, rac-(1R,6S)-6'-chloro-6-(3-chlorophenyl)-3-(4-methoxyphenyl)spiro[2-cyclohexene-1,3'-[3H]indole]-2',4(1'H)-dione, rac-(1S,6S)-6'-chloro-6-(3-chlorophenyl)-2-(2-ethoxyphenyl)spiro[2-cyclohexene-1,3'-[3H]indole]-2',4(1'H)-dione and rac-(1R,6S)-6'-chloro-6-(3-chlorophenyl)-3-(5-fluoro-2-methylphenyl)spiro[2-cyclohexene-1,3'-[3H]indole]-2',4(1'H)-dione.

6. The compound of claim 1 selected from the group consisting of (1R,6S)-6'-chloro-6-(3-chlorophenyl)-3-(2-methoxyphenyl)spiro[2-cyclohexene-1,3'-[3H]indole]-2',4(1'H)-dione, (1S,6R)-6'-chloro-6-(3-chlorophenyl)-3-(2-methoxyphenyl)spiro[2-cyclohexene-1,3'-[3H]indole]-2',4(1'H)-dione, rac-(1R,6S)-6'-chloro-6-(3-chlorophenyl)-3-(5-fluoro-2-hydroxyphenyl)spiro[2-cyclohexene-1,3'-[3H]indole]-2',4(1'H)-dione,
rac-(1R,6S)-6'-chloro-6-(3-chlorophenyl)-3-(4-fluoro-2-hydroxyphenyl)spiro[2-cyclohexene-1,3'-[3H]indole]-2',4(1'H)-dione,
rac-(1R,6S)-6'-chloro-3-(5-chloro-2-ethoxyphenyl)-6-(3-chlorophenyl)spiro[2-cyclohexene-1,3'-[3H]indole]-2',4(1'H)-dione,
rac-(1R,6S)-6'-chloro-6-(3-chlorophenyl)-3-(2-phenoxyphenyl)spiro[2-cyclohexene-1,3'-[3H]indole]-2',4(1'H)-dione,
rac-(1R,6S)-6'-chloro-3-(4-chloro-2-ethoxyphenyl)-6-(3-chlorophenyl)spiro[2-cyclohexene-1,3'-[3H]indole]-2',4(1'H)-dione,
rac-(1R,6S)-6'-chloro-3-(4-chloro-2-methoxyphenyl)-6-(3-chlorophenyl)spiro[2-cyclohexene-1,3'-[3H]indole]-2',4(1'H)-dione,
rac-(1R,6S)-6'-chloro-6-(3-chlorophenyl)-3-(2-ethoxy-5-methylphenyl)spiro[2-cyclohexene-1,3'-[3H]indole]-2',4(1'H)-dione,
rac-(1R,6S)-6'-chloro-6-(3-chlorophenyl)-3-[2-(trifluoromethoxy)phenyl)]spiro[2-cyclohexene-1,3'-[3H]indole]-2',4(1'H)-dione and
rac-(1R,6S)-6'-chloro-6-(3-chlorophenyl)-3-(3-furanyl)spiro[2-cyclohexene-1,3'-[3H]indole]-2',4(1'H)-dione.

7. A compound selected from the group consisting of
rac-(1R,6S)-6'-chloro-6-(3-chlorophenyl)-3-[4-(hydroxymethyl)phenyl]spiro[2-cyclohexene-1,3'-[3H]indole]-2',4(1'H)-dione,
rac-(1R,6S)-6'-chloro-6-(3-chlorophenyl)-3-(3,5-dimethyl-4-isoxazolyl)spiro[2-cyclohexene-1,3'-[3H]indole]-2',4(1'H)-dione,
rac-(1R,6S)-6'-chloro-6-(3-chlorophenyl)-3-(1-cyclohexenyl)spiro[2-cyclohexene-1,3'-[3H]indole]-2',4(1'H)-dione,
rac-(1R,6S)-6'-chloro-6-(3-chlorophenyl)-3-[2-(hydroxymethyl)phenyl]spiro[2-cyclohexene-1,3'-[3H]indole]-2',4(1'H)-dione,
rac-(1R,6S)-6'-chloro-6-(3-chlorophenyl)-3-[3-(hydroxymethyl)phenyl]spiro[2-cyclohexene-1,3'-[3H]indole]-2',4(1'H)-dione,
rac-(1S,6S)-6'-chloro-6-(3-chlorophenyl)-2-[3-(methoxycarbonyl)phenyl]spiro[2-cyclohexene-1,3'-[3H]indole]-2',4(1'H)-dione,
rac-(1R,6S)-6'-chloro-6-(3-chlorophenyl)-3-[3-(methoxycarbonyl)phenyl)]spiro[2-cyclohexene-1,3'-[3H]indole]-2',4(1'H)-dione,
rac-(1R,6S)-6'-chloro-6-(3-chlorophenyl)-2-[4-(methoxycarbonyl)phenyl]spiro[2-cyclohexene-1,3'-[3H]indole]-2',4(1'H)-dione,
rac-(1R,6S)-6'-chloro-6-(3-chlorophenyl)-3-[4-(methoxycarbonyl)phenyl]spiro[2-cyclohexene-1,3'-[3H]indole]-2',4(1'H)-dione,
rac-(1R,6S)-6'-chloro-3-(3-carboxyphenyl)-6-(3-chlorophenyl)spiro[2-cyclohexene-1,3'-[3H]indole]-2',4(1'H)-dione and
rac-(1S,6S)-6'-chloro-6-(3-chlorophenyl)-2-(3-cyanophenyl)spiro[2-cyclohexene-1,3'-[3H]indole]-2',4(1'H)-dione.

8. A compound selected from the group consisting of
rac-(1R,6S)-6'-chloro-6-(3-chlorophenyl)-3-(3-cyanophenyl)spiro[2-cyclohexene-1,3'-[3H]indole]-2',4(1'H)-dione,
rac-(1R,6S)-6'-chloro-6-(3-chlorophenyl)-2-(3-propoxyphenyl)spiro[2-cyclohexene-1,3'-[3H]indole]-2',4(1'H)-dione,
rac-(1R,6S)-6'-chloro-6-(3-chlorophenyl)-3-(3-propoxyphenyl)spiro[2-cyclohexene-1,3'-[3H]indole]-2',4(1'H)-dione,
rac-(1R,6S)-6'-chloro-6-(3-chlorophenyl)-3-(3-methyl-5-t-butylphenyl)spiro[2-cyclohexene-1,3'-[3H]indole]-2',4(1'H)-dione,
rac-(1R,6S)-6'-chloro-6-(3-chlorophenyl)-3-(2,4,6-trimethylphenyl)spiro[2-cyclohexene-1,3'-[3H]indole]-2',4(1'H)-dione,
rac-(1R,6S)-6'-chloro-6-(3-chlorophenyl)-3-(4-t-butylphenyl)spiro[2-cyclohexene-1,3'-[3H]indole]-2',4(1'H)-dione,
rac-(1R,6S)-6'-chloro-6-(3-chlorophenyl)-2-(2-methoxy-3-pyridyl)spiro[2-cyclohexene-1,3'-[3H]indole]-2',4(1'H)-dione,
rac-(1R,6S)-6'-chloro-6-(3-chlorophenyl)-3-(2-methoxy-3-pyridyl)spiro[2-cyclohexene-1,3'-[3H]indole]-2',4(1'H)-dione,
rac-(1R,6S)-6'-chloro-6-(3-chlorophenyl)-3-(3-BOC-aminophenyl)spiro[2-cyclohexene-1,3'-[3H]indole]-2',4(1'H)-dione,
rac-(1R,6S)-6'-chloro-6-(3-chlorophenyl)-2-(2,6-dihydro-2H-BOC-pyridyl)spiro[2-cyclohexene-1,3'-[3H]indole]-2',4(1'H)-dione,
rac-(1R,6S)-6'-chloro-6-(3-chlorophenyl)-3-(2,6-dihydro-2H-BOC-pyridyl)spiro[2-cyclohexene-1,3'-[3H]indole]-2',4(1'H)-dione,
rac-(1R,6S)-6'-chloro-6-(3-chlorophenyl)-3-(2-formylphenyl)spiro[2-cyclohexene-1,3'-[3H]indole]-2',4(1'H)-dione,
rac-(1R,6S)-6'-chloro-6-(3-chlorophenyl)-3-(3,5-bistrifluoromethylphenyl)spiro[2-cyclohexene-1,3'-[3H]indole]-2',4(1'H)-dione,
rac-(1R,6S)-6'-chloro-6-(3-chlorophenyl)-2-(2-ethylenephenyl)spiro[2-cyclohexene-1,3'-[3H]indole]-2',4(1'H)-dione,
rac-(1R,6S)-6'-chloro-6-(3-chlorophenyl)-3-(2-ethylenephenyl)spiro[2-cyclohexene-1,3'-[3H]indole]-2',4(1'H)-dione,
rac-(1R,6S)-6'-chloro-6-(3-chlorophenyl)-2-(3-methylthiophenyl)spiro[2-cyclohexene-1,3'-[3H]indole]-2',4(1'H)-dione,
rac-(1R,6S)-6'-chloro-6-(3-chlorophenyl)-3-(3-methylthiophenyl)spiro[2-cyclohexene-1,3'-[3H]indole]-2',4(1'H)-dione,
rac-(1R,6S)-6'-chloro-6-(3-chlorophenyl)-2-(3-dimethylacetamidophenyl)spiro[2-cyclohexene-1,3'-[3H]indole]-2',4(1'H)-dione,
rac-(1R,6S)-6'-chloro-6-(3-chlorophenyl)-3-(3-3-dimethylacetamido phenyl)spiro[2-cyclohexene-1,3'-[3H]indole]-2',4(1'H)-dione and
rac-(1R,6S)-6'-chloro-6-(3-chlorophenyl)-3-(3,4-dimethylphenyl)spiro[2-cyclohexene-1,3'-[3H]indole]-2',4(1'H)-dione.

9. A pharmaceutical composition comprising a compound of the formula

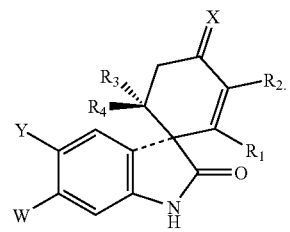

wherein
X is oxygen or hydrogen/hydroxy,
W is selected from the group consisting of hydrogen, halogen, cyano, nitro, ethynyl and cyclopropyl, Y is hydrogen or fluorine, $R_1$ is hydrogen, $R_2$ is selected from the group consisting of lower alkoxyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl, $R_3$ and $R_4$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl and substituted cycloalkenyl, with the proviso that one of $R_3/R_4$ is hydrogen and the other not hydrogen, or a pharmaceutically acceptable salt or ester thereof together with a pharmaceutically acceptable carrier or excipient.

* * * * *